United States Patent
Bae et al.

(10) Patent No.: US 12,332,244 B2
(45) Date of Patent: Jun. 17, 2025

(54) COMPOSITION FOR DIAGNOSING DISEASES ASSOCIATED WITH COX2 OVEREXPRESSION AND SCREENING METHOD THEREFOR

(71) Applicant: KYUNGPOOK NATIONAL UNIVERSITY INDUSTRY-ACADEMIC COOPERATION FOUNDATION, Daegu (KR)

(72) Inventors: Jae-Sung Bae, Daegu (KR); Hee Kyung Jin, Daegu (KR); Ju Youn Lee, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 1140 days.

(21) Appl. No.: 16/972,492

(22) PCT Filed: Jun. 4, 2019

(86) PCT No.: PCT/KR2019/006751
§ 371 (c)(1),
(2) Date: Dec. 4, 2020

(87) PCT Pub. No.: WO2019/235824
PCT Pub. Date: Dec. 12, 2019

(65) Prior Publication Data
US 2021/0270834 A1 Sep. 2, 2021

(30) Foreign Application Priority Data
Jun. 8, 2018 (KR) .................. 10-2018-0066312

(51) Int. Cl.
*G01N 33/573* (2006.01)
*G01N 33/574* (2006.01)
*G01N 33/68* (2006.01)

(52) U.S. Cl.
CPC ..... *G01N 33/573* (2013.01); *G01N 33/57484* (2013.01); *G01N 33/6896* (2013.01); *G01N 2333/90274* (2013.01)

(58) Field of Classification Search
CPC .......... G01N 33/573; G01N 33/57484; G01N 33/6896; G01N 2333/90274; G01N 33/60; G01N 2500/04; G01N 2500/20; A61K 51/0474
See application file for complete search history.

(56) References Cited

U.S. PATENT DOCUMENTS

2009/0112120 A1* 4/2009 Lee .................. C12Q 1/68
600/572
2021/0003594 A1* 1/2021 Bae .................. G01N 33/68

FOREIGN PATENT DOCUMENTS

EP 3769758 A1 1/2021
KR 10-1999-0064310 A 7/1999

OTHER PUBLICATIONS

Hsu, C. K., Lee, I. T., Lin, C. C., Hsiao, L. D., & Yang, C. M. (2015). Sphingosine-1-phosphate mediates COX-2 expression and PGE2/IL-6 secretion via c-Src-dependent AP-1 activation. Journal of cellular physiology, 230(3), 702-715. (Year: 2015).*
Maziere, B., & Loc'h, C. (1986). Radiopharmaceuticals labelled with bromine isotopes. International Journal of Radiation Applications and Instrumentation. Part A. Applied Radiation and Isotopes, 37(8), 703-713. (Year: 1986).*
Bielawska, A., & Hannun, Y. A. (2000). Preparation of radiolabeled ceramides and phosphosphingolipids. In Methods in enzymology (vol. 311, pp. 499-518). Academic Press. (Year: 2000).*
Lee, J. Y., Han, S. H., Park, M. H., Song, I. S., Choi, M. K., Yu, E., & Bae, J. S. (2020). N-AS-triggered SPMs are direct regulators of microglia in a model of Alzheimer's disease. Nature Communications, 11(1), 2358. (Year: 2020).*
Crian, G., Moldovean-Cioroianu, N. S., Timaru, D. G., Andrie, G., Cainap, C., & Chi, V. (2022). Radiopharmaceuticals for PET and SPECT imaging: A literature review over the last decade. International Journal of Molecular Sciences, 23(9), 5023. (Year: 2022).*
Prabhakaran, J., Molotkov, A., Mintz, A., & Mann, J. J. (2021). Progress in PET imaging of neuroinflammation targeting COX-2 enzyme. Molecules, 26(11), 3208. (Year: 2021).*
Kuge Y, Katada Y, Shimonaka S, Temma T, Kimura H, Kiyono Y, Yokota C, Minematsu K, Seki K, Tamaki N, Ohkura K, Saji H. Synthesis and evaluation of radioiodinated cyclooxygenase-2 inhibitors as potential SPECT tracers for cyclooxygenase-2 expression. Nucl Med Jan;33(1):21-7. doi:10.1016/j.nucmedbio.2005 (Year: 2006).*
Meadowcroft, M. D., Zhang, S., Liu, W., Park, B. S., Connor, J. R., Collins, C. M., . . . & Yang, Q. X. Direct magnetic resonance imaging of histological tissue samples at 3.0 T. Magnetic Resonance in Medicine: An Official Journal of the International Society for Magnetic Resonance in Medicine, 5 (Year: 2007).*
Szweda, M., Rychlik, A., Babińska, I., & Pomianowski, A. (2019). Significance of cyclooxygenase-2 in oncogenesis. Journal of Veterinary Research, 63(2), 215. (Year: 2019).*
Minghetti, L. (2004). Cyclooxygenase-2 (COX-2) in inflammatory and degenerative brain diseases. Journal of Neuropathology & Experimental Neurology, 63(9), 901-910. (Year: 2004).*

(Continued)

Primary Examiner — Sarah Alawadi
(74) Attorney, Agent, or Firm — James S. Keddie; Bozicevic, Field & Francis LLP

(57) ABSTRACT

A composition for diagnosing diseases associated with COX2 overexpression, containing a compound with a structural feature of exhibiting strong binding activity to a COX2 protein; and a screening method therefor.

7 Claims, 9 Drawing Sheets
Specification includes a Sequence Listing.

(56) References Cited

OTHER PUBLICATIONS

National Center for Biotechnology Information (2024). PubChem Compound Summary for CID 5280335, Sphingosine. Retrieved Feb. 1, 2024 from https://pubchem.ncbi.nlm.nih.gov/compound/Sphingosine. (Year: 2024).*

Subbaramaiah, K., Chung, W, & Dannenberg, A. J. Ceramide regulates the transcription of cyclooxygenase-2: evidence for involvement of extracellular signal-regulated kinase/c-Jun N-terminal kinase and p38 mitogen-activated protein kinase pathways. Journal of Biological Chemistry, 273(49), 32943-3294 (Year: 1998).*

Abe, A., Shayman, J. A., & Radin, N. S. (1996). A novel enzyme that catalyzes the esterification of N-acetylsphingosine: metabolism of C2-ceramides. Journal of Biological Chemistry, 271(24), 14383-14389. (Year: 1996).*

"NCBI" National Center for Biotechnology Information (2024). PubChem Compound Summary for CID 5497136, N-acetylsphingosine. Retrieved Jun. 25, 2024 from https://pubchem.ncbi.nlm.nih.gov/compound/N-acetylsphingosine. (Year: 2024).*

"Lincs" 184B5—Cell Line—HMS Lincs Database—HMS Lincs Project. (n.d.). Lincs.hms.harvard.edu. Retrieved Jun. 25, 2024, from https://lincs.hms.harvard.edu/db/cells/50576/ (Year: 2024).*

Amaravani et al., "COX-2 structural analysis and docking studies with gallic acid structural analogues", SpringerPlus, 2012, 1:58; pp. 1-7.

Lee et al., "Neuronal SphK1 acetylates COX2 and contributes to pathogenesis in a model of Alzheimer's Disease", Nature Communications, 2018, vol. 9, article No. 1479, pp. 1-14.

NCBI, GenBank Accession No. AAA57317.1 cyclooxygenase-2 [*Homo sapiend*], 1994, pp. 1-2.

Nekkaz et al., "Docking Studies on Cyclooxygenases-2 Inhibitors based on Potential Ligand Binding Sites", International Journal of Computer Applications (0975-8887), 2014, 87(1): 27-34.

\* cited by examiner

| | $V_{max}$ | $K_M$ | $K_{cat}$ | $K_{cat}/K_M$ | % Relative $K_{cat}/K_M$ |
|---|---|---|---|---|---|
| ● COX2 | 67.29 pmol/min | 46.01 μM | 0.48 min$^{-1}$ | 0.010522 | 100 |
| ○ COX2 S565A | 47.76 pmol/min | 65.45 μM | 0.34 min$^{-1}$ | 0.00525 | 49.9 |
| ▼ COX2 N181A | 58.49 pmol/min | 47.71 μM | 0.42 min$^{-1}$ | 0.008819 | 83.8 |
| △ COX2 T564A | 62.56 pmol/min | 46.52 μM | 0.45 min$^{-1}$ | 0.009675 | 91.9 |
| ■ COX2 S567A | 61.82 pmol/min | 50.59 μM | 0.44 min$^{-1}$ | 0.008792 | 83.5 |

| PK parameter (Brain) | N-Acetyl sphingosine | |
|---|---|---|
| | p.o.10 mg/kg | i.v.1 mg/kg |
| $AUC_{last}$ (ng·h/mL) | 895.32±60.53 | 1344.94±224.29 |
| $C_{max}$ (ng/mL) | 90.27±2.95 | 165.18±18.42 |
| $T_{1/2}$ (h) | 21.99±6.07 | 6.31±0.38 |
| MRT (h) | 8.64±1.01 | 6.94±0.62 |
| Brain distribution | 3.18 | 2.16 |

COMPOSITION FOR DIAGNOSING DISEASES ASSOCIATED WITH COX2 OVEREXPRESSION AND SCREENING METHOD THEREFOR

CROSS-REFERENCE TO RELATED APPLICATIONS

This application is a § 371 national phase of International Application No. PCT/KR2019/006751, filed on Jun. 4, 2019, which claims the benefit of Korean Patent Application No. 10-2018-0066312, filed on Jun. 8, 2018, which applications are incorporated by reference herein.

TECHNICAL FIELD

This application claims the priority of Korean Patent Application No. 10-2018-0066312, filed on Jun. 8, 2018, the entirety of which is a reference of the present application.

The present invention relates to a composition for diagnosing diseases associated with cyclooxygenase 2 (COX2) overexpression and a screening method therefor and, more particularly, to a composition for diagnosing diseases associated with COX2 overexpression containing a compound with a structural feature of exhibiting strong binding activity to a COX2 protein, and a screening method therefor.

BACKGROUND ART

Inflammatory diseases are closely associated with most of diseases, and as a result of basic research in molecular and cellular immunology, methods for diagnosing, treating and preventing diseases based on such immunology have been dramatically changed. One example of this is the discovery of an inducible form of a cyclooxygenase (COX) enzyme. A COX protein was first purified in 1976, and constitutive cyclooxygenase (COX) cloned in 1988 was found to act in the synthesis of prostaglandin (PGs) from arachidonic acid (AA). After 3 years of such purification, an inducible enzyme having COX activity was identified and named as COX2, while the constitutive COX was named as COX1.

The expression of COX2 is under the regulation of pro-inflammatory cytokines and growth factors. Thus, it is widely known up to now that COX2 acts on the regulation of both inflammation and cell growth. The COX2 is induced in many tissues and simultaneously shown structurally in the brain and spinal cord, wherein the COX2 acts on nerve transmission for pain and fever. The two subtypes of COX are almost similar in structure, but have important differences in selectivity of a substrate and an inhibitor and intracellular locations thereof. Protective prostaglandin (PG), which preserves the shape of the gastric mucosa and maintains normal renal function in the damaged kidney, is synthesized by COX1. On the other hand, PG synthesized by COX2 in immune cells plays a very important role in the inflammatory process.

COX2 in a normal state is known to mediate various physiological phenomena such as immune responses, but it has been reported that abnormal overexpression or overactivation of COX2 is closely associated with the occurrence and development of various diseases.

Specifically, the COX2 is overexpressed in most of acute or chronic inflammatory diseases and very closely associated with the development process of the diseases, and it has been reported that the expression of the COX2 is increased in cancer tissues compared to normal tissues in most of human cancers including bladder cancer, breast cancer, colon cancer, liver cancer, lung cancer, prostate cancer and stomach cancer (Koga et al., 1999; Lim H Y et al., 2000; Soslow et al., 2000; Yoshimura et al., 2000; Yoshimura et al., 2001). In addition, it has been reported that the expression of the COX2 is increased in various diseases, such as neuroinflammatory disease, Alzheimer's disease, Parkinson's disease (PNAS, Apr. 29, 2003, vol. 100, no. 9, 5473-5478), amyotrophic lateral sclerosis (European Journal of Neuroscience, Vol 18, pp. 1527-1534, 2003), traumatic brain injury (JOURNAL OF NEUROTRAUMA Volume 17, Number 8, 2000 695-711), ischemia (1294-1299, PNAS, Jan. 30, 2001, vol. 98, no. 3), etc.

In particular, according to the research results of the present inventors, it was confirmed that in the case of degenerative neurological diseases including Alzheimer's, the brain expression of the COX2 protein was rapidly increased from a very early stage before observable symptoms of the diseases were expressed.

Therefore, if a substance capable of detecting the expression level of the COX2 protein very quickly and accurately is developed, it will be very useful in diagnosis and prognosis prediction of various diseases associated with COX2 overexpression. Particularly, if such a substance can exhibit a high distribution in the brain by passing through a brain-blood barrier (BBB), it will be possible to diagnose early neurodegenerative diseases, in which rapid detection of the diseases is most important.

DETAILED DESCRIPTION OF THE INVENTION

Technical Problem

Accordingly, the present inventors have made many efforts to develop a diagnostic substance capable of not only exhibiting direct binding activity to a COX2 protein, but also quickly and accurately detecting diseases associated with the COX2 overexpression including inflammatory brain diseases due to excellent BBB permeability. As a result, the present inventors have found that substances interacting directly with specific amino acids of the COX2 protein exhibit very high binding force to the COX2 protein to be very useful in the diagnosis of associated diseases, and completed the present invention.

Therefore, an object of the present invention is to provide a composition for diagnosing diseases associated with COX2 overexpression comprising a compound containing a functional group that interacts with at least one amino acid selected from the group consisting of N181, T564, S567, and S565 of a cyclooxygenase 2 (COX2) protein defined by SEQ ID NO: 1.

Further, an object of the present invention is to provide a composition for diagnosing diseases associated with COX2 overexpression consisting of a compound containing a functional group that interacts with at least one amino acid selected from the group consisting of N181, T564, S567, and S565 of a COX2 protein defined by SEQ ID NO: 1.

Further, an object of the present invention is to provide a composition for diagnosing diseases associated with COX2 overexpression consisting essentially of a compound containing a functional group that interacts with at least one amino acid selected from the group consisting of N181, T564, S567, and S565 of a COX2 protein defined by SEQ ID NO: 1.

Another object of the present invention is to provide a screening method of a diagnostic substance for diseases associated with COX2 overexpression comprising the steps of: (a) contacting a test substance with a COX2 protein defined by SEQ ID NO: 1; (b) measuring whether the test substance interacts with at least one amino acid selected from the group consisting of N181, T564, S567 and S565 of the COX2 protein defined by SEQ ID NO: 1; and (c) selecting a substance that interacts with the COX2 protein in step (b).

Yet another object of the present invention is to provide use of a compound containing a functional group that interacts with at least one amino acid selected from the group consisting of N181, T564, S567, and S565 of a cyclooxygenase 2 (COX2) protein defined by SEQ ID NO: 1 to prepare an agent for diagnosing diseases associated with COX2 overexpression.

Still another object of the present invention is to provide a method for diagnosing diseases associated with COX2 overexpression comprising the steps of:
a) obtaining a biological sample from a subject suspected of having the diseases associated with COX2 overexpression;
b) administering a compound containing a functional group that interacts with at least one amino acid selected from the group consisting of N181, T564, S567, and S565 of a cyclooxygenase 2 (COX2) protein defined by SEQ ID NO: 1 to the sample;
c) measuring whether the administered compound interacts with the COX2 protein in the sample in step b); and
d) comparing the degree of interaction between the COX2 protein and the compound in comparison with that of a normal control group, and diagnosing the subject as having the diseases associated with COX2 overexpression when the degree of interaction between the COX2 protein and the compound is increased as compared with that of the normal control group.

Technical Solution

In order to achieve the object of the present invention, the present invention provides a composition for diagnosing diseases associated with COX2 overexpression comprising a compound containing a functional group that interacts with at least one amino acid selected from the group consisting of N181, T564, S567, and S565 of a cyclooxygenase 2 (COX2) protein defined by SEQ ID NO: 1.

Further, the present invention provides a composition for diagnosing diseases associated with COX2 overexpression consisting of a compound containing a functional group that interacts with at least one amino acid selected from the group consisting of N181, T564, S567, and S565 of a COX2 protein defined by SEQ ID NO: 1.

Further, the present invention provides a composition for diagnosing diseases associated with COX2 overexpression consisting essentially of a compound containing a functional group that interacts with at least one amino acid selected from the group consisting of N181, T564, S567, and S565 of a COX2 protein defined by SEQ ID NO: 1.

In order to achieve another object of the present invention, the present invention provides a screening method of a diagnostic substance for diseases associated with COX2 overexpression comprising the steps of: (a) contacting a test substance with a COX2 protein defined by SEQ ID NO: 1; (b) measuring whether the test substance interacts with at least one amino acid selected from the group consisting of N181, T564, S567 and S565 of the COX2 protein defined by SEQ ID NO: 1; and (c) selecting a substance that interacts with the COX2 protein in step (b).

In order to achieve yet another object of the present invention, the present invention provides use of a compound containing a functional group that interacts with at least one amino acid selected from the group consisting of N181, T564, S567, and S565 of a cyclooxygenase 2 (COX2) protein defined by SEQ ID NO: 1 to prepare an agent for diagnosing diseases associated with COX2 overexpression.

In order to achieve still another object of the present invention, the present invention provides a method for diagnosing diseases associated with COX2 overexpression comprising the steps of:
a) obtaining a biological sample from a subject suspected of having the diseases associated with COX2 overexpression;
b) administering a compound containing a functional group that interacts with at least one amino acid selected from the group consisting of N181, T564, S567, and S565 of a cyclooxygenase 2 (COX2) protein defined by SEQ ID NO: 1 to the sample;
c) measuring whether the administered compound interacts with the COX2 protein in the sample in step b); and
d) comparing the degree of interaction between the COX2 protein and the compound in comparison with that of a normal control group, and diagnosing the subject as having the diseases associated with COX2 overexpression when the degree of interaction between the COX2 protein and the compound is increased as compared with that of the normal control group.

Hereinafter, the present invention will be described in detail.

The present invention provides a composition for diagnosing diseases associated with COX2 overexpression comprising a compound containing a functional group that interacts with at least one amino acid selected from the group consisting of N181, T564, S567, and S565 of a COX2 protein defined by SEQ ID NO: 1.

Further, the present invention provides a composition for diagnosing diseases associated with COX2 overexpression consisting of a compound containing a functional group that interacts with at least one amino acid selected from the group consisting of N181, T564, S567, and S565 of a COX2 protein defined by SEQ ID NO: 1, and a composition for diagnosing diseases associated with COX2 overexpression consisting essentially of the compound.

According to an embodiment of the present invention, it was conformed that compounds exhibiting strong binding force to COX2 to the same degree as arachidonic acid, a substrate of COX2, form hydrogen bonds with N181, T564, and S567 of the COX2 protein defined by SEQ ID NO: 1, and interact through a nucleophilic acyl substitution reaction with S565.

According to another embodiment of the present invention, after preparing a mutant COX2 protein in which asparagine (N181), threonine (T564), or serine (S567, S565) capable of forming hydrogen bonds as polar amino acids is substituted with alanine (A), a non-polar amino acid, it has been compared which level a compound of the present invention, which strongly binds to wild-type COX2, can exhibit the binding force with each mutant COX2. As a result, it was confirmed that the binding force between the mutant COX2 in which any one amino acid selected from the group consisting of N181, T564, S567, and S565 was substituted with alanine and the compound of the present invention was significantly lower than that of the wild-type COX2.

Such a result means that at least one amino acid selected from the group consisting of N181, T564, S567, and S565 in the COX2 protein defined by SEQ ID NO: 1 plays a very important role in binding to a compound having a specific structure. That is, it is meant that the compound that interacts with at least one amino acid selected from the group consisting of N181, T564, S567 and S565 of the COX2 protein defined by SEQ ID NO: 1 exhibits the activity of binding directly to COX2 to be used for diagnosing diseases associated with the overexpression of the COX2 protein.

In the present invention, an amino acid sequence of the COX2 protein defined by SEQ ID NO: 1 is as follows

```
(SEQ ID NO: 1):
mlaralllca  vlalshtanp  ccshpcqnrg  vcmsvgfdqy kcdctrtgfy  gencstpefl  triklflkpt  pntvhyilth fkgfwnvvnn  ipflrnaims  yvltsrshli  dspptynady gyksweafsn  lsyytralpp  vpddcptplg  vkgkkqlpds neivekllr   rkfipdpqgs  nmmfaffaqh  fthqffktdh krgpaftngl  ghgvdlnhiy  getlarqrkl  rlfkdgkmky qiidgemypp  tvkdtqaemi  yppqvpehlr  favgqevfgl vpglmmyati  wlrehnrvcd  vlkqehpewg  deqlfqtsrl iligetikiv  iedyvqhlsg  yhfklkfdpe  llfnkqfqyq nriaaefntl  yhwhpllpdt  fqihdqkyny  qqfiynnsil lehgitqfve  sftrqiagrv  aggrnvppav  qkvsqasidq srqmkyqsfn  eyrkrfmlkp  yesfeeltge  kemsaeleal ygdidavely  pallvekprp  daifgetmve  vgapfslkgl mgnvicspay  wkpstfggev  gfqiintasi  qslicnnvkg cpftsfsvpd  peliktvtin  asssrsgldd  inptvllker stel
```

In the present invention, the "interaction" may be understood as including all physical and chemical binding relationships, substitution reactions, etc. that may be formed between functional groups, and a kind thereof is not particularly limited. Non-limiting examples thereof may include ionic bonds, covalent bonds, van der Waals bonds, hydrogen bonds, nucleophilic substitution reactions, electrophilic addition reactions, and the like.

Preferably, the interaction may be a bond or interaction between a specific functional group contained in the compound of the present invention and a hydroxyl group or amine group of the polar amino acid (asparagine, threonine or serine) contained in the COX2 protein. More preferably, the interaction may be a van der Waals bond, a hydrogen bond or a nucleophilic acyl substitution reaction, and most preferably a hydrogen bond or a nucleophilic acyl substitution reaction.

Meanwhile, in the compound of the present invention, the "specific structure" means having (i) a functional group capable of forming a hydrogen bond with at least one amino acid selected from the group consisting of N181, T564 and S567 of the COX2 protein, or (ii) a functional group capable of having a nucleophilic acyl substitution reaction with S565.

In the present invention, the "functional group" refers to an atomic group having a commonly chemical property in an organic compound, and is a cause of imparting the properties of the compound. In the present invention, the compound may contain at least one functional group capable of forming a hydrogen bond with at least one amino acid selected from the group consisting of N181, T564 and S567 of the COX2, and may contain at least one functional group capable of having a nucleophilic acyl substitution reaction with S565.

That is, the compound of the present invention may contain (i) at least one functional group capable of forming a hydrogen bond with at least one amino acid selected from the group consisting of N181, T564 and S567 of the COX2 protein, or (ii) at least one functional group capable of having a nucleophilic acyl substitution reaction with S565.

Preferably, the compound of the present invention may contain (i) at least one functional group capable of forming a hydrogen bond with at least one amino acid selected from the group consisting of N181, T564 and S567 of the COX2 protein, and (ii) at least one functional group capable of having a nucleophilic acyl substitution reaction with S565.

More preferably, the compound of the present invention may contain (i) at least one functional group capable of forming a hydrogen bond with N181, T564 and S567 of the COX2 protein, and (ii) at least one functional group capable of having a nucleophilic acyl substitution reaction with S565.

In the compound of the present invention, a kind of functional group capable of forming a hydrogen bond with at least one amino acid selected from the group consisting of N181, T564 and S567 of the COX2 protein defined by SEQ ID NO: 1 is not particularly limited, but preferably, may be a hydroxyl or amine group. Asparagine (N), threonine (T), or serine (S), which is a polar amino acid, forms a hydrogen bond with the hydroxyl group or amine group contained in the compound to maintain strong binding force.

In the present invention, the functional group capable of having the nucleophilic acyl substitution reaction may be acid halide, acid anhydride, ester, or amide, preferably ester or amide. The carbonyl carbon of the functional group contained in the compound of the present invention binds directly to oxygen or nitrogen with strong electronegativity to act as an electrophile, and the hydroxyl group or amine group of the polar amino acid contained in the COX2 protein acts as a nucleophile so that the nucleophilic acyl substitution reaction may occur.

When the compound of the present invention contains (i) at least one functional group capable of forming a hydrogen bond with at least one amino acid selected from the group consisting of N181, T564 and S567 of the COX2 protein, or (ii) at least one functional group capable of having a nucleophilic acyl substitution reaction with S565, preferably, all of these functional groups may bind to carbon, nitrogen or oxygen within 5 atoms, and more preferably, all of these functional groups may bind to carbon, nitrogen or oxygen within 3 atoms.

In particular, according to an embodiment of the present invention, since the compound capable of forming a hydrogen bond with at least one amino acid selected from the group consisting of N181, T564 and S567 of the COX2 protein defined by SEQ ID NO: 1 or interacting with S565 through a nucleophilic acyl substitution reaction may bind strongly to the COX2 protein without affecting a binding site of arachidonic acid, which is a substrate of COX2, it is preferable in that the compound does not block a normal physiological reaction of COX2, so that side effects may not occur.

The present invention also provides a composition for diagnosing diseases associated with COX2 overexpression comprising a compound defined by the following Chemical Formula 1 or a pharmaceutically acceptable salt thereof as a compound capable of interacting with at least one amino acid selected from the group consisting of N181, T564, S567 and S565 of a COX2 protein defined by SEQ ID NO: 1:

[Chemical Formula 1]

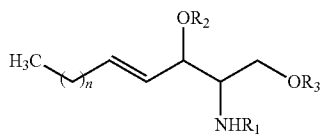

Wherein,
$R_1$ is hydrogen or $C_1$-$C_7$ alkylcarbonyl,
$R_2$ and $R_3$ are each independently hydrogen, $C_1$-$C_7$ alkylcarbonyl, or

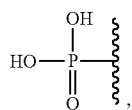

and
n is an integer of 5 to 15.
Preferably,
$R_1$ is hydrogen or $C_1$-$C_3$ alkylcarbonyl,
$R_2$ and $R_3$ are each independently hydrogen, $C_1$-$C_3$ alkylcarbonyl, or

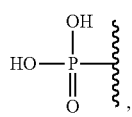

and
n is an integer of 7 to 14.
However, at least one of $R_1$, $R_2$ and $R_3$ is $C_1$-$C_3$ alkylcarbonyl.
More preferably,
$R_1$ is hydrogen or an acetyl group,

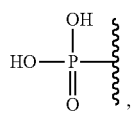

$R_2$ and $R_3$ are each independently hydrogen, an acetyl group, or, and
n is an integer of 7 to 13.
However, at least one of $R_1$, $R_2$ and $R_3$ is an acetyl group.
Much more preferably,
$R_1$ and $R_2$ are each independently hydrogen or an acetyl group,
$R_3$ is hydrogen, an acetyl group or

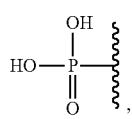

and
n is an integer of 7 to 13.
However, at least one of $R_1$, $R_2$ and $R_3$ is an acetyl group.
Most preferably,
$R_1$ and $R_2$ are each independently hydrogen or an acetyl group,
$R_3$ is hydrogen, an acetyl group or

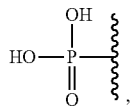

and
n is an integer of 7 to 12.
However, at least one of $R_1$, $R_2$ and $R_3$ is an acetyl group.
In the present invention, the "alkylcarbonyl" refers to a structure in which a carbonyl group (C=O) binds to an alkyl group. In the present invention, the "acetyl group" refers to alkylcarbonyl in which alkyl is methyl.
In the present invention, the "alkyl" refers to a saturated, aliphatic hydrocarbon group containing a straight or branched carbon chain having 1 to 6 carbon atoms.
In the present invention, the compound defined by Chemical Formula 1 above may be prepared as a pharmaceutically acceptable salt or a solvate according to a general method in the art, and the form of such a salt is also included in the scope of Chemical Formula 1 above of the present invention.
Meanwhile, as the salt of the compound defined by Chemical Formula 1 above, an acid addition salt formed by a pharmaceutically acceptable free acid is useful. The acid addition salt is prepared by a general method, for example, by dissolving the compound in an excess acid aqueous solution and precipitating the salt using a water-miscible organic solvent, such as methanol, ethanol, acetone or acetonitrile. The same molar amount of the compound and an acid or alcohol (e.g., glycol monomethyl ether) in water may be heated, and then the mixture may be evaporated and dried, or the precipitated salt may be suction-filtered.
At this time, as the free acid, organic acids and inorganic acids may be used. As the inorganic acids, hydrochloric acid, phosphoric acid, sulfuric acid, nitric acid, tartaric acid, etc. may be used, and as the organic acids, methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc. may be used, but the free acid is not limited thereto.
Further, bases may also be used to prepare pharmaceutically acceptable metal salts. An alkali metal salt or an alkaline earth metal salt may be obtained, for example, by dissolving the compound in a large amount of alkali metal hydroxide or alkaline earth metal hydroxide solution, filtering a non-dissolved compound salt, and then evaporating and drying a filtrate. In this case, the metal salt is pharmaceutically suitable to prepare, particularly, sodium, potassium or calcium salts, but is not limited thereto.
Further, a silver salt corresponding thereto may be obtained by reacting the alkali metal or alkaline earth metal salt with a suitable silver salt (e.g., silver nitrate).
The pharmaceutically acceptable salt of the compound defined by Chemical Formula 1 of the present invention includes salts of acidic or basic groups that may exist in the compound defined by Chemical Formula 1, unless otherwise indicated. For example, the pharmaceutically acceptable salt may include a sodium, potassium, calcium or magnesium salt having a hydroxyl group, and other pharmaceutically acceptable salts having an amino group include hydrobromide, sulfate, hydrogen sulfate, phosphate, hydrogen phosphate, dihydrogen phosphate, acetate, succinate, citrate, tartrate, lactate, mandelate, methanesulfonate (mesylate), and p-toluenesulfonate (tosylate) salts, which may be prepared through methods or processes for preparing salts known in the art.

In addition, when the compound defined by Chemical Formula 1 above has an asymmetric center, the compound may exist in different enantiomeric forms, and all optical isomers and R or S-type stereoisomers of the compound defined by Chemical Formula 1 and mixtures thereof are also within the scope of the present invention.

In the present invention, at least one atom of the compound defined by Chemical Formula 1 above may be a radioactive isotope. The radioactive isotope refers to an atom having an atomic mass or mass number different from an atomic mass or mass number typically found in nature. In the present invention, at least one atom of hydrogen, nitrogen, or carbon contained in the compound defined by Chemical Formula 1 above may be a radioactive isotope. That is, in the present invention, the hydrogen, nitrogen or carbon contained in the compound defined by Chemical Formula 1 above may be selected from the group consisting of $^2$H, $^3$H, $^{11}$C, $^{13}$C, $^{14}$C, $^{13}$N, $^{15}$N, $^{15}$O and $^{17}$O, respectively.

In addition, in the present invention, the compound defined by Chemical Formula 1 above may be $C_1$-$C_7$ alkylcarbonyl wherein at least one atom is a radioactive isotope in at least one selected from the group consisting of $R_1$, $R_2$ and $R_3$. In this case, the alkyl carbon of $R_1$, $R_2$ and/or $R_3$ may be $^{11}$C, $^{13}$C, and $^{14}$C and/or the carbonyl carbon may be $^{11}$C, $^{13}$C, and $^{14}$C, or the hydrogen of the alkyl group may be $^2$H or $^3$H, or the oxygen of the carbonyl group may be $^{15}$O or $^{17}$O. Preferably, the carbonyl carbon of $R_1$, $R_2$ and/or $R_3$ may be $^{11}$C, $^{13}$C, and $^{14}$C, more preferably, the carbonyl carbon of $R_1$, $R_2$ and/or $R_3$ may be $^{11}$C or $^{14}$C, and most preferably, the carbonyl carbon of $R_1$ may be $^{11}$C or $^{14}$C.

In addition, in the present invention, the compound defined by Chemical Formula 1 may be labeled with one or more radioactive isotopes selected from the group consisting of $^2$H, $^3$H, $^{11}$C, $^{13}$C, $^{14}$C, $^{13}$N, $^{15}$N, $^{15}$O, $^{17}$O, $^{18}$F, $^{35}$S, $^{36}$Cl, $^{82}$Br, $^{76}$Br, $^{77}$Br, $^{123}$I, $^{124}$I, $^{125}$I and $^{131}$I. The labeling with the radioactive isotope means that the atom contained in the compound of Chemical Formula 1 is replaced or substituted by the isotope. In the present invention, the radioactive isotope labeled in the compound defined by Chemical Formula 1 above may vary depending on a specific application of the compound.

The isotope-labeling of the compound of the present invention may be performed according to methods known in the art, and for example, may be prepared by mixing $^2$H, $^3$H, $^{11}$C, $^{13}$C, $^{14}$C, $^{13}$N, $^{15}$N, 15, 17O, $^{18}$F, $^{35}$S, $^{36}$Cl, $^{82}$Br, $^{76}$Br, $^{77}$Br, $^{123}$I, $^{124}$I, $^{125}$I or $^{131}$I into the compound of the present invention. This is achieved by placing a reagent into a source of radioactivity such as a nuclear reactor, a cyclotron, or the like to use a reagent that makes one or more of the atoms contained therein radioactive. Additionally, many isotopically labeled reagents, such as $^2$H$_2$O, $^3$H$_3$Cl, $^{14}$C$_6$H$_5$Br, ClCH$_2$$^{14}$COCl, and the like, are commercially available.

The present invention also provides a diagnostic composition, characterized in that the compound of Chemical Formula 1 above is selected from the group consisting of compounds defined by the following Chemical Formulas 2 to 11:

[Chemical Formula 2]

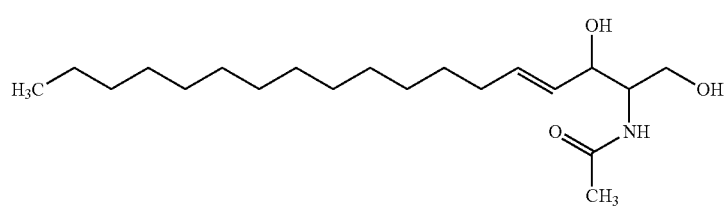

[Chemical Formula 3]

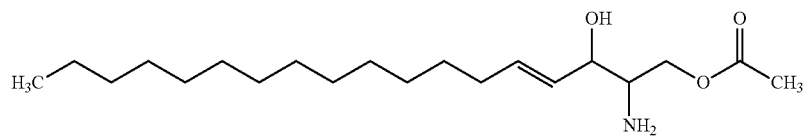

[Chemical Formula 4]

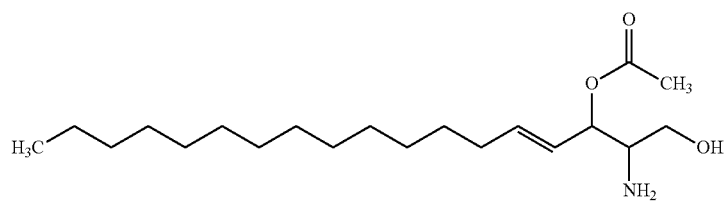

[Chemical Formula 5]

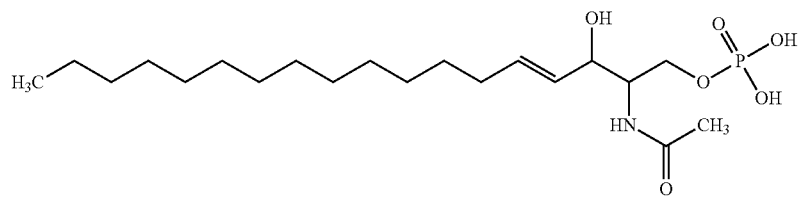

[Chemical Formula 6]

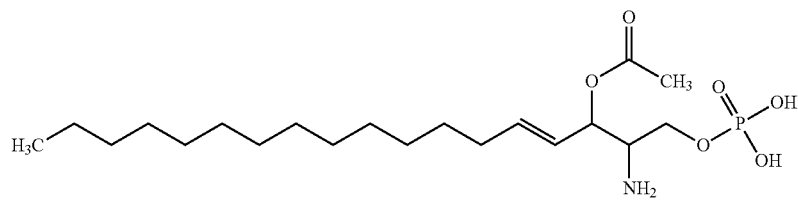

[Chemical Formula 7]

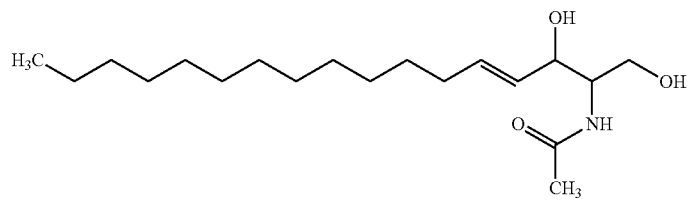

[Chemical Formula 8]

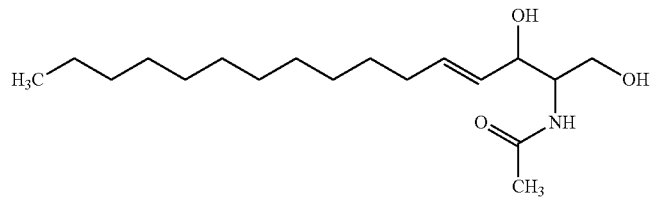

[Chemical Formula 9]

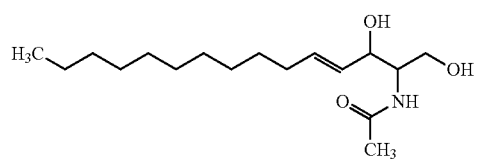

[Chemical Formula 10]

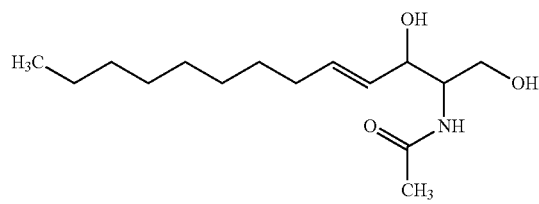

[Chemical Formula 11]

Any atom contained in the compounds defined by Chemical Formulas 2 to 11 above of the present invention may be a radioactive isotope. That is, hydrogen, nitrogen or carbon contained in the compounds defined by Chemical Formulas 2 to 11 above may be selected from the group consisting of $^{2}H$, $^{3}H$, $^{11}C$, $^{13}C$, $^{14}C$, $^{13}N$, $^{15}N$, $^{15}O$ and $^{17}O$, respectively. A detailed description of the radioactive isotope is as described above.

Preferably, any carbon contained in the compounds defined by Chemical Formulas 2 to 11 above may be $^{11}C$, $^{13}C$, or $^{14}C$, more preferably, carbon (i.e., alkyl carbon or carbonyl carbon) contained in an acetyl group of each compound may be $^{11}C$, $^{13}C$, or $^{14}C$, and most preferably, the carbonyl carbon included in the acetyl group may be $^{11}C$, $^{13}C$, or $^{14}C$.

In addition, the compounds defined by Chemical Formulas 2 to 11 above may be labeled with one or more radioactive isotopes selected from the group consisting of $^{2}H$, $^{3}H$, $^{11}C$, $^{13}C$, $^{14}C$, $^{13}N$, $^{15}N$, $^{15}O$, $^{17}O$, $^{18}F$, $^{35}S$, $^{36}Cl$, $^{82}Br$, $^{76}Br$, $^{77}Br$, $^{123}I$, $^{124}I$, $^{125}I$ and $^{131}I$. A detailed description of the method of labeling the radioactive isotope on each of the compounds, etc. is as described above.

The diagnostic composition of the present invention may further include any biocompatible carrier in addition to the compound of the present invention that binds to COX2. The "biocompatible carrier" is a fluid, particularly a liquid, in which the compound according to the present invention is suspended or dissolved so that the composition can be administered into a mammalian body so as to have physiologically drug tolerance, that is, without toxicity or excessive discomfort. The biocompatible carrier may be suitably an injectable carrier liquid, such as a sterile, pyrogen-free injection; aqueous solutions such as saline (preferably, a final product for injection may be in a balanced state so as not to be isotonic or storable); and aqueous solutions of one or more tension modulating substances (e.g., salts of plasma cations with biocompatible counterions), sugars (e.g., glucose or sucrose), sugar alcohols (e.g., sorbitol or mannitol), glycols (e.g., glycerol), or other nonionic polyol substances (e.g., polyethylene glycol, propylene glycol, etc.). The biocompatible carrier may also include biocompatible organic solvents such as ethanol. These organic solvents are useful for solubilizing more lipophilic compounds or formulations. Preferably, the biocompatible carrier may be a pyrogen-free injection, an isotonic saline, or an aqueous ethanol solution. The pH of the biocompatible carrier for intravenous injection may suitably be 4.0 to 10.5.

Meanwhile, in the present invention, the diagnostic composition may be detected by various means, and the means for detecting a radioactive isotope may be appropriately selected by a person skilled in the art according to a type of radioisotope contained or labeled in the compound of the present invention. For example, the isotopes may be detected using imaging techniques, photographic films or scintillation counters, and may be applied to preferably imaging techniques, more preferably positron emission tomography (PET), single photon emission computed tomography (SPECT), or magnetic resonance imaging (MRI) to be applied to image the COX2 protein in a pathological site.

That is, the diagnostic composition of the present invention is administered orally or parenterally to mammals including humans, and then may be in contact with COX2 expressed in the body to bind directly to COX2 through the body, preferably through the brain via a blood-brain barrier. Thereafter, the compound of the present invention binding to COX2 reaches a specific time point to be detectable, and a signal emitted from the radioactive isotope contained or labeled in the compound of the present invention may be detected by the PET, SPECT or MRI technique.

In the present invention, the diseases associated with COX2 overexpression are diseases accompanying the overexpression of the COX2 protein, and may be selected from the group consisting of an inflammatory disease, a neurodegenerative disease, traumatic brain injury, cancer, and ischemia.

In the present invention, the neurodegenerative disease may be selected from the group consisting of Alzheimer's disease, Parkinson's disease, Niemann's disease, amyotrophic lateral sclerosis, multiple sclerosis, neuroblastoma, stroke, Lou Gehrig's disease, Huntington's disease, Creutzfeldt-Jakob disease, post-traumatic stress disorder, depression, schizophrenia, and spinal muscular atrophy, but is not limited thereto.

In the present invention, the inflammatory disease may be selected from the group consisting of inflammatory bowel disease, peritonitis, osteomyelitis, cellulitis, pancreatitis, trauma-induced shock, bronchial asthma, allergic rhinitis, cystic fibrosis, acute bronchitis, chronic bronchitis, acute bronchiolitis, chronic bronchiolitis, osteoarthritis, gout, spondyloarthropathy, ankylosing spondylitis, Reiter's syndrome, psoriatic arthrosis, intestinal spondylitis, juvenile arthritis, juvenile ankylosing spondylitis, reactive arthritis, infectious arthritis, post-infectious arthritis, gonococcal arthritis, tuberculous arthritis, viral arthritis, fungal arthritis, syphilitic arthritis, Lyme disease, arthritis associated with vasculitis syndrome, polyarteritis nodosa, irritable vasculitis, Lou Gehrig's granulomatosis, polymyalgia rheumatica, joint cell arteritis, calcium crystal deposition arthropathy, pseudogout, non-articular rheumatism, bursitis, tendonitis, epicondylitis (tennis elbow), neuropathic joint disease, hemarthrosic, Henoch-Scherein purpura, hypertrophic osteoarthropathy, multicentric reticular histiocytoma, scoliosis, hemoglobinosis, hemoglobinopathy, hyperlipoproteinemia, hypogammaglobulinemia, familial mediterranean fever, Behat's disease, systemic lupus erythematosus, recursive fever, multiple sclerosis, sepsis, septic shock, acute respiratory distress syndrome, multiple organ failure, chronic obstructive pulmonary disease, rheumatoid arthritis, acute lung injury, broncho-pulmonary dysplasia, and inflammatory skin disease, but is not limited thereto.

In the present invention, the cancer may be selected from the group consisting of breast cancer, colon cancer, lung cancer, small cell lung cancer, stomach cancer, liver cancer, blood cancer, bone cancer, pancreatic cancer, skin cancer, head or neck cancer, melanoma in the skin or eye, eye tumor, peritoneal cancer, uterine cancer, ovarian cancer, rectal cancer, anal cancer, colon cancer, fallopian tube carcinoma, endometrial carcinoma, cervical cancer, vaginal cancer, vulval carcinoma, Hodgkin's disease, esophageal cancer, small intestine cancer, endocrine cancer, thyroid cancer, parathyroid cancer, adrenal cancer, soft tissue sarcoma, urethral cancer, penile cancer, prostate cancer, testicular cancer, oral cancer, gallbladder cancer, bile duct cancer, chronic or acute leukemia, lymphocytic lymphoma, bladder cancer, kidney cancer, ureteral cancer, renal cell carcinoma (neuroblastoma), renal pelvic carcinoma, CNS tumor, primary CNS lymphoma, spinal cord tumor, brainstem glioma and pituitary adenoma, but is not limited thereto.

The present invention provides a screening method of a diagnostic substance for diseases associated with COX2 overexpression comprising the steps of: (a) contacting a test substance with a COX2 protein defined by SEQ ID NO: 1; (b) measuring whether the test substance interacts with at least one amino acid selected from the group consisting of N181, T564, S567 and S565 of the COX2 protein defined by SEQ ID NO: 1; and (c) selecting a substance that interacts with the COX2 protein in step (b).

The "test substance" used while referring to the screening method of the present invention means an unknown substance used in screening to examine whether the test substance interacts with at least one amino acid selected from the group consisting of N181, T564, S567 and S565 of the COX2 protein defined by SEQ ID NO: 1 or binds to the COX2 protein.

In the screening method of the present invention, the binding between the COX2 protein defined by SEQ ID NO: 1 and the test substance is measured in an environment treated with the test substance. The measurement of binding may be performed by various methods known in the art, and as a result of the measurement, when the binding between the COX2 protein defined by SEQ ID NO: 1 and the test substance is significantly formed, the test substance may be determined as a diagnostic substance of diseases associated with COX2 overexpression.

In the screening method of the present invention, the "measurement" means encompassing a series of deductive and inductive processes that derive an unknown value by using specific data, and is used in the same meaning as calculation, prediction, identification, and determination. Accordingly, the term measurement in the present invention includes all of experimental measurement, computational calculation on in silico, and establishment of a relationship between multiple variables based thereon.

In step (a) of the present invention, the contacting of the test substance with the COX2 protein defined by SEQ ID NO: 1 means directly treating the test substance to cells or tissues expressing the COX2 protein, or includes virtually contacting a structure of the test substance with a molecular structure model of the COX2 protein defined by SEQ ID NO: 1 on a computational simulation.

According to an embodiment of the present invention, step (b) may be performed using a computational simulation.

In the present invention, the "computational simulation" means a simulation of predicting and reproducing the behavior of a specific system through mathematical modeling using one or multiple computing equipment constituting a network. More specifically, the computational simulation may be a molecular dynamic simulation. The molecular dynamic simulation is a computational simulation that numerically calculates the trajectories of atoms or molecules according to established physical laws and reproduces their physical motions. According to the present invention, the present inventors perform a molecular docking search and a molecular dynamic simulation for the compound exhibiting strong binding force to the COX2 protein defined by SEQ ID NO: 1 and the COX2 protein to examine structural features of the interaction between the COX2 protein and the compound. As a result, it is confirmed that a substance that interacts with at least one amino acid selected from the group consisting of N181, T564, S567 and S565 of the COX2 protein defined by SEQ ID NO: 1 may exhibit very high binding force to the COX2 protein.

In the screening method, a detailed description of "the interaction of the test substance with at least one amino acid selected from the group consisting of N181, T564, S567 and S565 of the COX2 protein defined by SEQ ID NO: 1" may refer to those described above.

Meanwhile, in the present invention, after step (c), the screening method may further include administering the selected test substance to a COX2 overexpression animal model and then comparing the test substance with a control to compare a detection level in the animal model.

This step is a step of confirming whether a substance confirmed to interact with at least one amino acid selected from the group consisting of N181, T564, S567 and S565 of the COX2 protein defined by SEQ ID NO: 1 may bind to the COX2 protein even in an actual in vivo experiment through a computational simulation. Whether there is a possibility to be developed as an actual diagnostic substance may be further searched by additionally confirming in vivo kinetics of the test substance, whether to pass through the BBB, and pharmacokinetic properties through such an animal experiment.

In the present invention, the control means a substance known to have activity of binding to the COX2 protein, and a kind thereof is not particularly limited.

The present invention provides use of a compound containing a functional group that interacts with at least one amino acid selected from the group consisting of N181, T564, S567, and S565 of a cyclooxygenase 2 (COX2) protein defined by SEQ ID NO: 1 to prepare an agent for diagnosing diseases associated with COX2 overexpression.

The present invention provides a method for diagnosing diseases associated with COX2 overexpression comprising:
  a) obtaining a biological sample from a subject suspected of having the diseases associated with COX2 overexpression;
  b) administering a compound containing a functional group that interacts with at least one amino acid selected from the group consisting of N181, T564, S567, and S565 of a cyclooxygenase 2 (COX2) protein defined by SEQ ID NO: 1 to the sample;
  c) measuring whether the administered compound interacts with the COX2 protein in the sample in step b); and
  d) diagnosing the degree of interaction between the COX2 protein and the compound as the diseases associated with COX2 overexpression when the degree of interaction between the COX2 protein and the compound is increased as compared with a normal control.

In one embodiment, the present invention provides a method of diagnosing and treating diseases associated with COX2 overexpression comprising the steps of:
  a) obtaining a biological sample from a subject suspected of having the diseases associated with COX2 overexpression;
  b) administering an effective dose of compound containing a functional group that interacts with at least one amino acid selected from the group consisting of N181, T564, S567, and S565 of a cyclooxygenase 2 (COX2) protein defined by SEQ ID NO: 1 to the sample;
  c) measuring whether the administered compound interacts with the COX2 protein in the sample in step b);
  d) diagnosing the degree of interaction between the COX2 protein and the compound as the diseases associated with COX2 overexpression when the degree of interaction between the COX2 protein and the compound is increased as compared with a normal control; and
  e) administering a therapeutic drug for treating the diseases associated with COX2 overexpression to the diagnosed subject or treating the diseases through surgery.

Step e) is a step of performing the treatment of the diseases by a means such as administration of the therapeutic drug or surgery, to the subject in which the disease is diagnosed in step d).

The term 'treatment' of the present invention comprehensively refers to improving diseases associated with COX2 overexpression or symptoms of the diseases associated with COX2 overexpression, and may include treating or substantially preventing these diseases associated with COX2 overexpression, or improving the conditions thereof and includes alleviating, treating or preventing a symptom or most of symptoms derived from the diseases, but is not limited thereto.

The 'diseases associated with COX2 overexpression' may be inflammatory diseases, neurodegenerative diseases, traumatic brain injury, cancer, or ischemia as described above.

The type of 'therapeutic drug' is not particularly limited as long as the therapeutic drug is a drug used for the treatment of the diseases associated with COX2 overexpression, that is, inflammatory diseases, neurodegenerative diseases, traumatic brain injury, cancer, or ischemia. The therapeutic drug is administered to a subject in a 'therapeutically effective dose', and the therapeutically effective dose to a patient may be determined by those skilled in the art in consideration of various factors, such as the age, weight, health conditions, and gender of a patient, the severity of a disease, diet and excretion rate, etc. as well as unique properties, route of administration, and treatment number of times of a drug. The route of administration of the therapeutic drug is not particularly limited, and the therapeutic drug may be administered orally or parenterally, and the route of administration includes both local administration and systemic administration. The parenteral administration is not limited thereto, but may be, for example, intranasal drug application, subcutaneous injection, and the like, and as another example, a method such as intramuscular injection, intravenous injection, or the like may be used.

The 'biological sample' of the present invention is isolated and obtained from a subject suspected of having a disease, but is not limited thereto, but may be selected from the group consisting of cells, tissues, blood, serum, plasma, saliva, mucosa, and urine. The "subject" may be animals, preferably animals including mammals, particularly humans, and may be cells, tissues, organs, etc. derived from animals. The subject may be a patient requiring the therapeutic effects.

The term 'comprising' of the present invention is used in the same manner as 'containing' or 'characterizing', and does not exclude additional ingredients or steps of the method which are not mentioned in the composition or the method. The term 'consisting of' means excluding additional elements, steps or ingredients, etc., unless otherwise noted. The term 'consisting essentially of' means including ingredients or steps that do not substantially affect basic properties thereof in addition to the described ingredients or steps within the range of the composition or the method.

Advantageous Effects

The compound provided in the present invention not only has very excellent binding force with COX2, but also has very high blood-brain barrier (BBB) permeability, and can be very useful in diagnosing and predicting prognosis of diseases associated with COX2 overexpression including neurodegenerative diseases.

MODE FOR CARRYING OUT INVENTION

Figure 1:
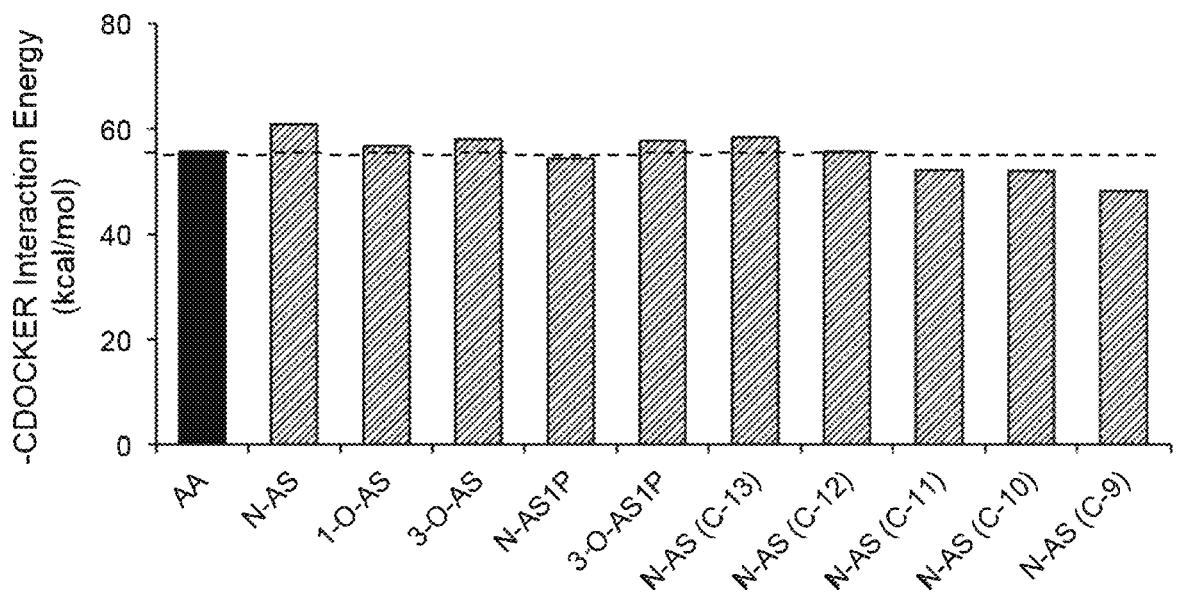
FIG. 1 is a diagram illustrating confirming and quantifying binding energy at which compounds according to the present invention directly bind to COX2 through a docking simulation.

Hereinafter, the present invention will be described in detail.

However, the following Examples are just illustrative of the present invention, and the contents of the present invention are not limited to the following Examples.

Experimental Materials and Experimental Methods

1. Compounds

The structures and names of compounds used in experiments in the present invention were shown below:

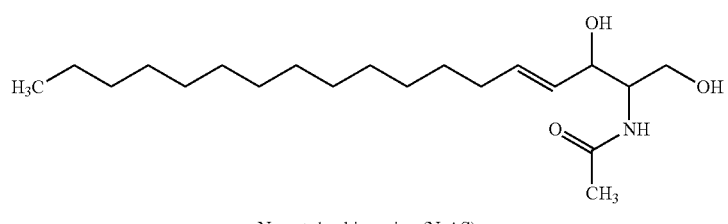

N-acetyl sphingosine (N-AS)

(1)

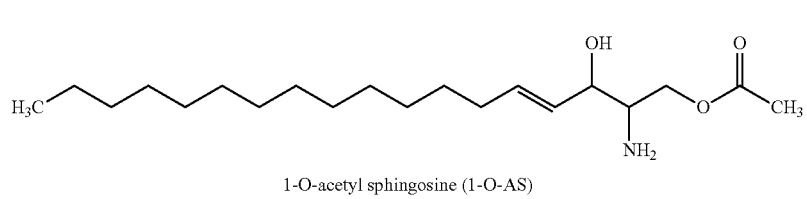

1-O-acetyl sphingosine (1-O-AS)

(2)

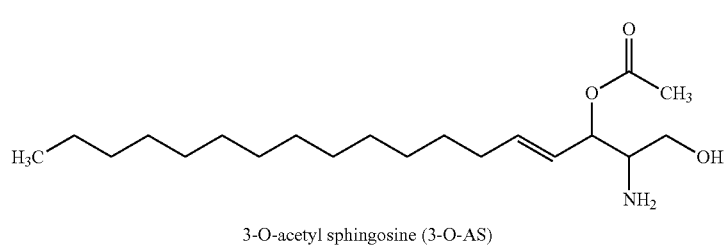

3-O-acetyl sphingosine (3-O-AS)

(3)

-continued

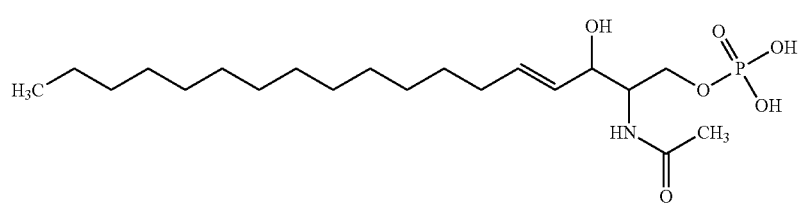

N-acetyl sphingosine-1-phosphate (N-AS1P)    (4)

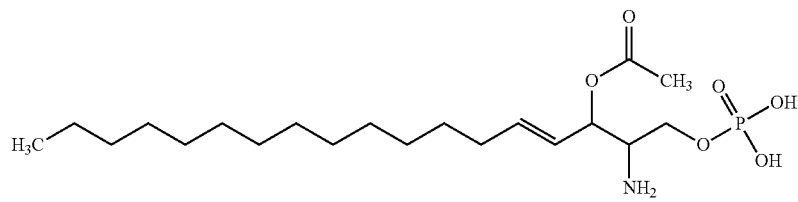

3-O-acetyl sphingosine-1-phosphate (3-O-AS1P)    (5)

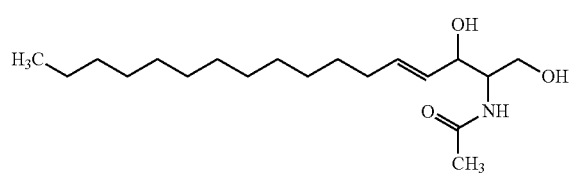

N-acetyl sphingosine derivative 1 (N-AS(C-13))    (6)

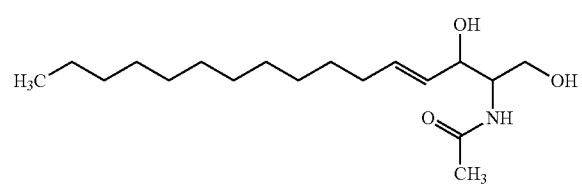

N-acetyl sphingosine derivative 2 (N-AS(C-12))    (7)

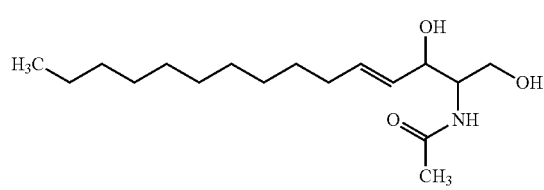

N-acetyl sphingosine derivative 3 (N-AS(C-11))    (8)

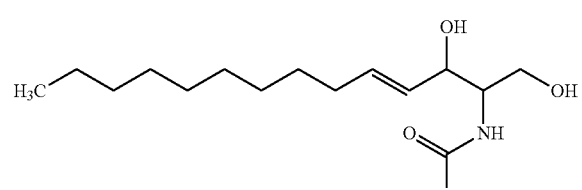

N-acetyl sphingosine derivative 4 (N-AS(C-10))    (9)

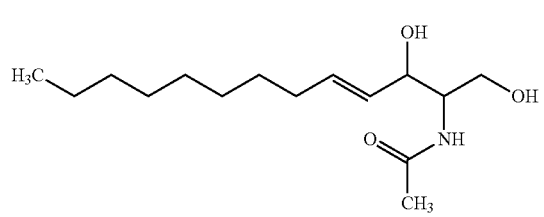

N-acetyl sphinosine derivative 5 (N-AS(C-9))    (10)

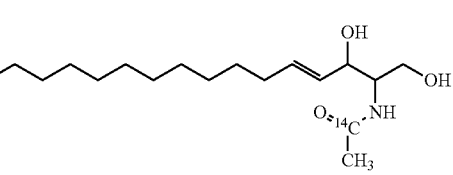

[$^{14}$C]N-acetyl sphingosine ([$^{14}$C]N-AS)    (11)

2. Docking Simulation

The three-dimensional structure of a COX2 protein (PDB code: 3HS5) and the molecular docking of each compound according to the present invention were analyzed using Discovery Studio 2018 implemented based on a DS-CDOCKER protocol. A docking position of the compound was simulated by designating a substrate binding site region including R106, Y341, Y371 and S516 of an amino acid sequence of a COX2 protein (GeneBank accession No.AAR23927.1). Arachidonic acid (AA), a substrate for COX2, was used as a positive control. A specific experimental method was performed with reference to Nat Commun. 2018 Jan. 9; 9(1):128, etc.

3. Enzymatic Analysis of COX2

The binding activity of wild type COX2 or mutant COX2 (N181A, T564A, S565A, S567A) and N-acetyl sphingosine (N-AS) was analyzed by filter binding assay (Nat Commun. 2018 Apr. 16; 9(1):1479).

The binding rate (Vbinding) of [$^{14}$C]N-acetyl sphingosine (American Radiolabeled Chemicals, ARC1024) to wild-type COX2 and mutant COX2 (N181A, T564A, S565A, S567A) was expressed as the concentration of N-acetyl sphingosine. The nonlinear regression analysis of a saturation plot showed the binding activity of N-acetyl sphingosine and wild-type COX2 or mutant COX2 (N181A, T564A, S565A, S567A) using $K_{cat}$ (catalyst constant) and $K_M$ (Michaelis- Menten constant). By using the calculated $K_{cat}$ and $K_M$, $K_{cat}/K_M$ (catalytic efficiency), which has been widely used as a measure of enzyme performance, was calculated from wild-type COX2 and mutant-type COX2 (N181A, T564A, S565A, S567A).

4. Mouse

Mouse experiments have been approved by the Kyungpook National University Institutional Animal Care and Use Committee (IACUC). A transgenic mouse line overexpressing APPswe (hAPP695swe) or PS1 (presenilin-1M146V) based on $C_{57}BL/6$ mice (Charles River, UK) was used [Hereinafter, "APP mouse": refers to a mouse overexpressing APPswe, "PS1 mouse": refers to a mouse overexpressing presenilin-1M146V; GlaxoSmithKline]

5. Immunofluorescence

Microglia were isolated from the cerebrum of a 3-month-old, 5-month-old or 9-month-old wild type or APP/PS1 mouse, treated with anti-COX2 (rabbit, 1:10, Abcam) and anti-CX3CR1 (mouse, 1:100, Biolegend) antibodies, and then cultured. The microglia were quantified and analyzed for the percentage of cells stained with anti-COX2 among all microglia using an Operetta CLS High-Content Analysis System (PerkinElmer, USA).

6. Method of Measuring Binding Degree Between COX2 and [$^{14}$C]

After oral administration of 10 μCi of [$^{14}$C]N-acetyl sphingosine (American Radiolabeled Chemicals, ARC1024) to 5-month-old wild-type and APP/PS1 mice, microglia were isolated from the cerebra of the mice after 1 hour.

In addition, neuroblastoma SH-SY5Y was treated with 2 μCi of [$^{14}$C]N-acetyl sphingosine (American Radiolabeled Chemicals, ARC1024) for 1 hour, and then cells were collected.

The COX2 protein of isolated microglia and neuroblastoma SH-SY5Y were isolated by immunoprecipitation, and then liquid scintillation counting was performed on [$^{14}$C].

7. Western Blot

The expression of the proteins was analyzed using Western blotting. First, antibodies against COX2 (abcam) and β-actin (Santa Cruz) were used, and the densitometric quantification was performed using ImageJ software (US National Institutes of Health).

8. Statistical Analysis

A T-test of students was performed to compare two groups, while for comparison of multiple groups, repeated measurement analysis of a Tukey's HSD test and a variance test was performed according to an SAS statistical package (release 9.1; SAS Institute Inc., Cary, NC). *$p<0.05$, $p<0.01$, and *$p<0.001$ were considered significant.

Experimental Results

1. Confirming that Compounds of the Present Invention Bind Directly to COX2

The docking simulation was performed to confirm whether the compounds of the present invention listed in the experimental methods directly bind to COX2, and the binding energy of these compounds to COX2 was compared with the binding energy of arachidonic acid, a substrate of COX2, to COX2.

The result thereof was illustrated in FIG. 1.

As illustrated in FIG. 1, it was confirmed that the binding energy of COX2 and arachidonic acid (AA) and the binding energy of the compounds according to the present invention to COX2 had similar values.

That is, it was found that the compounds of the present invention can bind to COX2 well in the same level as that arachidonic acid (AA), a substrate of COX2, binds to COX2.

2. Confirmation of New Binding Site of N-Acetyl Sphingosine (N-AS) to COX2

Referring to "Experimental Result 1", it was confirmed that among 10 kinds of compounds applied in the experiment, the N-acetyl sphingosine (N-AS) compound exhibited the highest binding energy with COX2.

Accordingly, the present inventors selected the N-AS compound and analyzed the docking simulation result to confirm the structural characteristics of these compounds binding to COX2.

Figure 2:
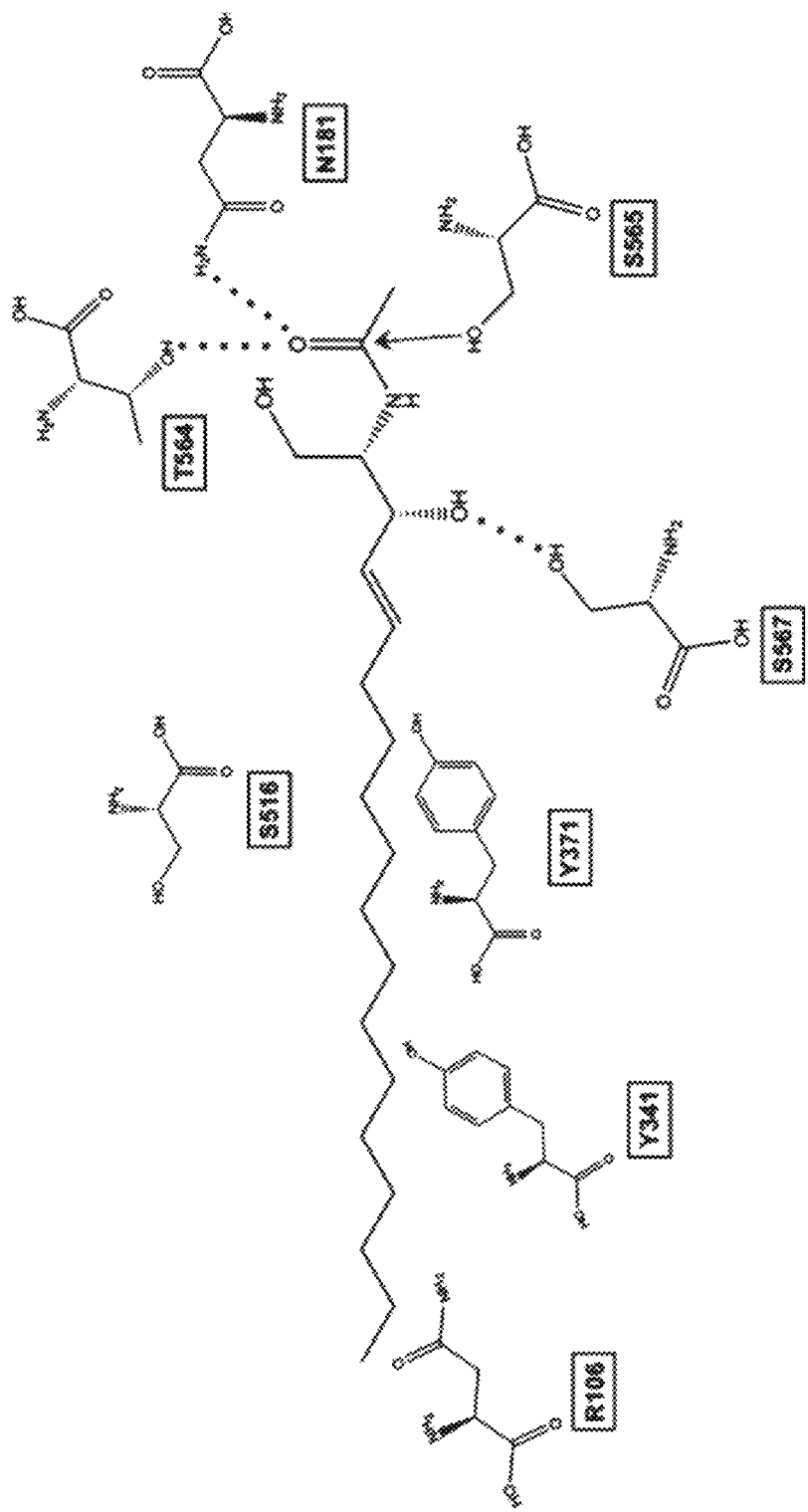
FIG. 2 is a schematic diagram illustrating that N-acetyl sphingosine (N-AS) directly binds to COX2 through hydrogen bonds with N181, T564, and S567 of a COX2 protein and a nucleophilic interaction with S565.

The result thereof was illustrated in FIG. 2.

As illustrated in FIG. 2, it was confirmed that the N-AS bound to COX2 through hydrogen bonds (FIG. 2, dotted lines) with N181, T564, and S567 of the COX2 protein, and through these hydrogen bonds, S565 had a nucleophilic acyl substitution reaction (arrow). In addition, it was confirmed that a site at which the N-AS bound to COX2 included a binding site (R106, Y341, Y371, S516) of arachidonic acid (AA), a substrate of COX2 known in the related art (FIG. 2).

3. Confirmation of Binding Degree of N-Acetyl Sphingosine (N-AS) to COX2

In "Experimental Result 2", it was confirmed that the positions of N181, T564, S567 and S565 of the COX2 protein played a very important role in binding to N-AS through a docking simulation.

Accordingly, the present inventors attempted to confirm once again through an enzymatic analysis method that a hydrogen bond at each amino acid position of the COX2 protein played an important role in binding to N-AS.

That is, after preparing a mutant COX2 protein in which asparagine (N181), threonine (T564), or serine (S567, S565) capable of forming a hydrogen bond as a polar amino acid was substituted with alanine (A), a non-polar amino acid, which level of the binding activity to the N-AS was exhibited was compared by comparing each mutant COX2 with wild-type COX2.

Figure 3:
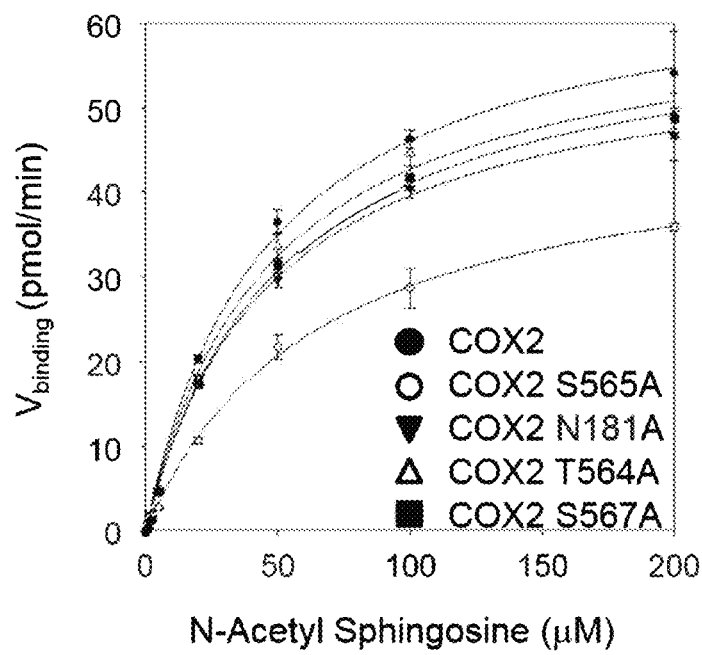
FIG. 3 illustrates a result of evaluating the degree of binding between N-acetyl sphingosine and wild type COX2 or mutant COX2 (M181A, T564A, S565A or S567A).

The result thereof was illustrated in FIG. 3.

As illustrated in FIG. 3, the binding of the N-AS to the wild-type COX2 was saturated as the concentration of N-AS increased, and the $K_M$ and $K_{cat}$ values were 46.01 μm and 0.48 min-1, respectively. Through this, it was confirmed once again that the N-AS bound well to the COX2.

On the other hand, in the case of mutant COX2 (N181A, T564A, S565A and S567A) in which the amino acid at the N-AS binding site of COX2 confirmed in "Experiment 2" was substituted with alanine, it was confirmed that when the catalytic efficiency ($K_{cat}/K_M$), which was widely used as a measure of enzyme performance, was compared with the catalytic efficiency of the wild-type COX2, the catalytic efficiency of the mutant COX2 decreased compared to the wild-type COX2. Among them, it was confirmed that when S565 was mutated, the catalytic efficiency decreased the most, and these results showed that the N-AS directly bound to the COX2 protein through the hydrogen bonds with N181, T564, S565, and S567 of COX2 and the nucleophilic acyl substitution reaction.

Therefore, it was found that a compound capable of having the hydrogen bonds with N181, T564, S565, and S567 of COX2 and the nucleophilic acyl substitution reaction may strongly bind to COX2.

4. Confirmation of Brain Distribution of N-Acetyl Sphingosine

The present inventors have confirmed that the compounds of the present invention are very excellent in binding activity to COX2 through "Experimental Result 1". Therefore, it could be determined that these compounds could be used for diagnosis of various diseases caused by overexpression of the COX2 protein. In particular, it was confirmed whether the compounds of the present invention could be used for degenerative brain diseases in which the COX2 protein is overexpressed.

In order to apply the compounds of the present invention to the diagnosis of degenerative brain diseases, it is important to distribute the compounds well to the brain after administration. To confirm this, the N-AS was administered orally (10 mg/kg) or through tail vein (1 mg/kg), and then the brain was extracted by time to measure the concentration of N-AS, and after 24 hours, the brain was extracted to measure the concentration of the remaining N-AS.

The result thereof was illustrated in FIG. 4.

Figure 4A:
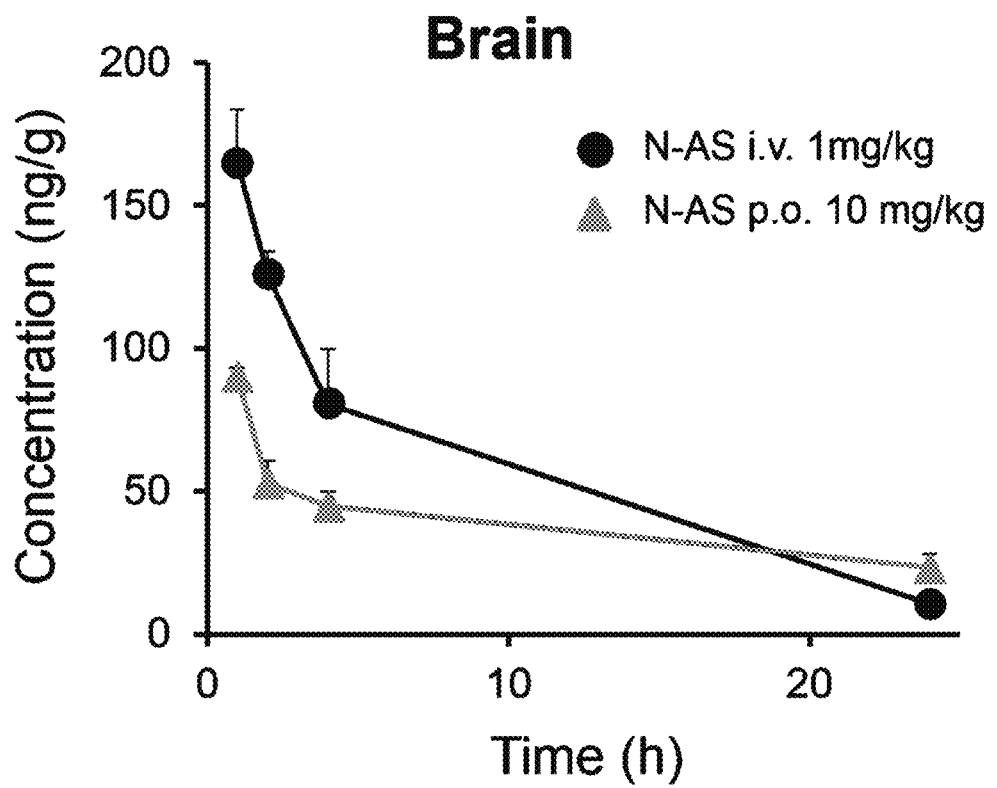
FIGS. 4A to 4C illustrate a result of showing a concentration remaining in the brain for each time period after oral (p.o. 10 mg/kg) or intravenous administration (i.v. 1 mg/kg) of N-acetyl sphingosine to normal mice (FIG. 4A), a result of showing a concentration remaining in the brain after 24 hours (FIG. 4B), and a pharmacokinetic test analysis result for a brain distribution (FIG. 4C) (n=3/group).
Figure 4B:
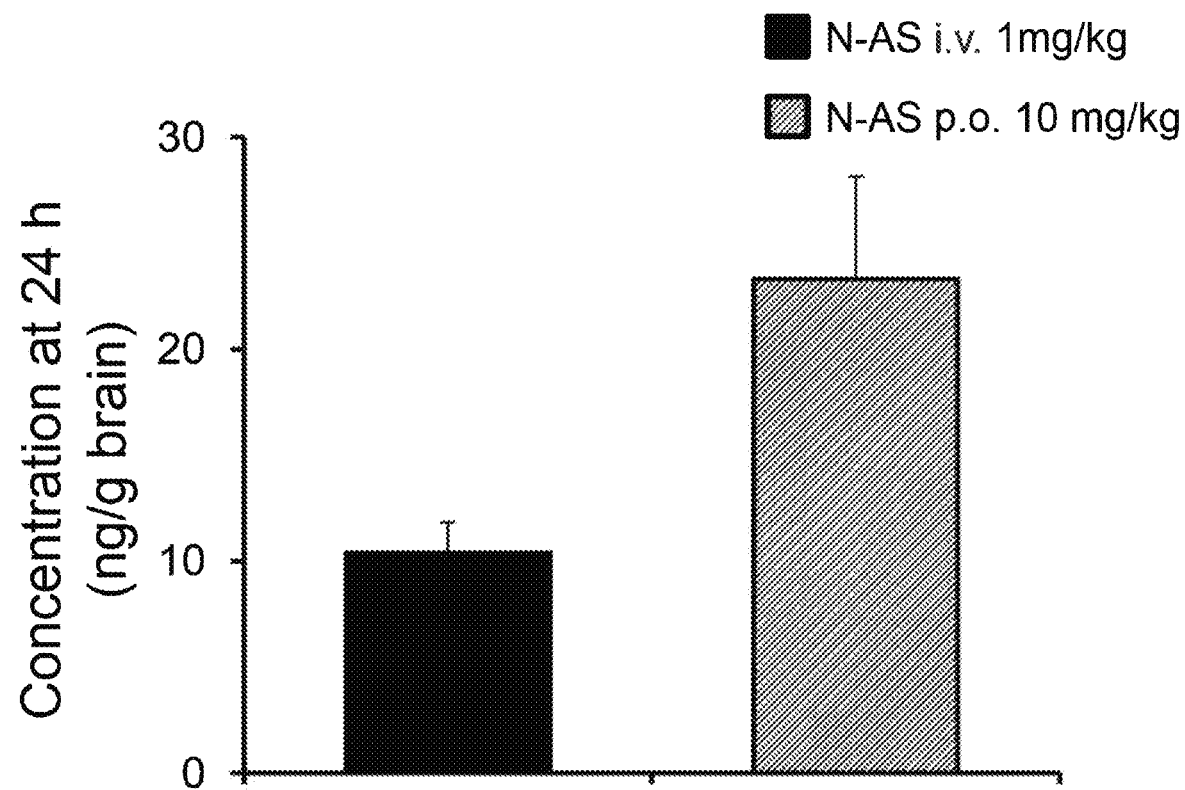
Figures 4C, 5:
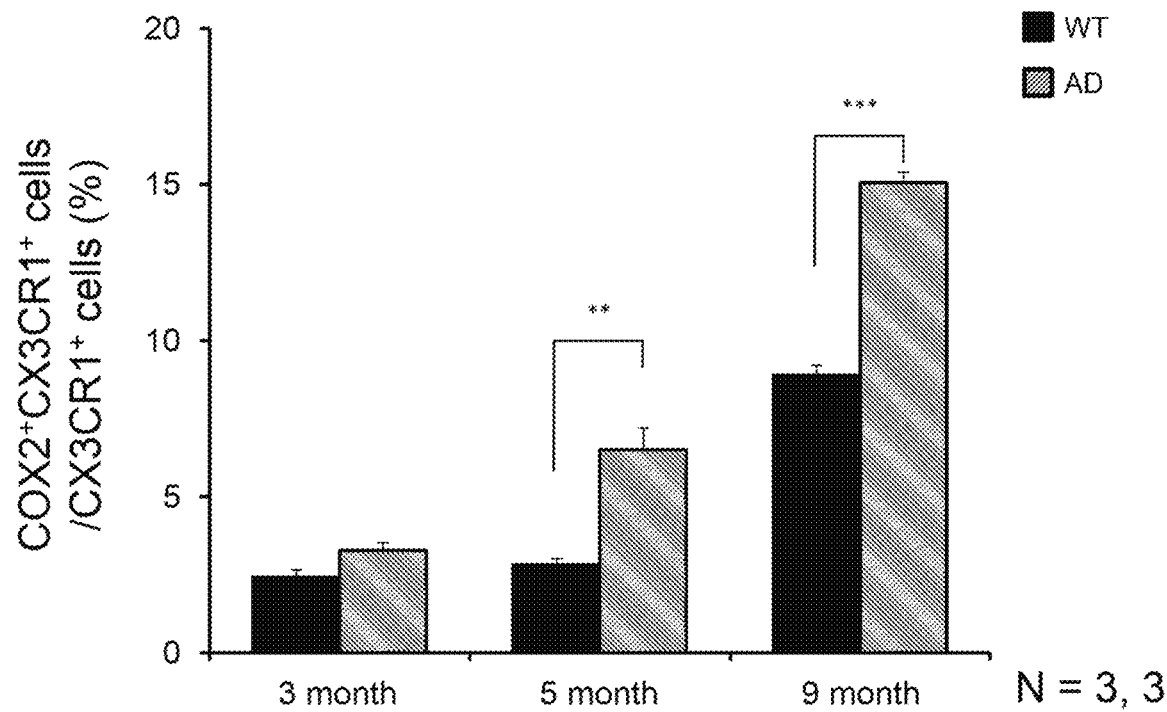
FIG. 5 illustrates a result of confirming expression levels of COX2 protein in microglia (CX3CR1$^+$) derived from wild-type or APP/PS1 mice at 3 months, 5 months and 9 months (WT: wild type, AD: Alzheimer's animal model).

As a result, it was confirmed that the concentration of N-AS was high in the brain (FIGS. 4A and 4B). On the other hand, as a result of confirming pharmacokinetic parameters in the brain, it was confirmed that the brain distribution value was 3.18 for oral administration and 2.16 for tail vein administration (FIG. 4C).

From these results, it can be seen that the N-AS exhibits a high brain distribution in terms of pharmacokinetics to be very usefully used in the development of diagnostic substances for brain diseases such as neurodegenerative diseases.

5. Confirming that COX2 Expression in Microglia was Increased from the Early Stage of Alzheimer's According to previous studies, it has been reported that the expression level of COX2 protein was increased in brain microglia of patients with degenerative neuroinflammatory diseases including Alzheimer's (Curr Neuropharmacol. 2010 March; 8(1): 62-68).

The present inventors confirmed from when the COX2 expression in microglia increased in an Alzheimer's environment.

As a result, it was confirmed that the COX2 expression in microglia was significantly increased from 5 months, which was an early stage of the occurrence of Alzheimer's, compared with a control as illustrated in FIG. 5.

Through the results, it was confirmed that the COX2 expression in microglia was increased from the early stage of the occurrence of Alzheimer's, and it could be determined that the compounds of the present invention, which have excellent brain distribution and direct binding activity with the COX2 protein, may be used for diagnosis or prognosis prediction from the early stage of Alzheimer's.

6. Confirming that COX2 Expression in Microglia was Increased from the Early Stage of Occurrence of Alzheimer's by Using the Compound of the Present Invention The present inventors confirmed that the expression of the COX2 protein in brain microglia was increased from the early stage of the occurrence of Alzheimer's in "Experimental Result 5", and then attempted to determine whether the increased expression of the COX2 protein may be directly detected in the Alzheimer's brain using the compounds of the present invention.

In other words, [$^{14}$C]N-acetyl sphingosine ([$^{14}$C]N-AS), in which carbon of N-AS which strongly bound to COX2 and had a brain distribution was substituted with an isotope, was administered orally (10 µCi) to a 5-month-old Alzheimer's animal model. After 1 hour, the COX2 in microglia was isolated from the control and the Alzheimer's animal model by immunoprecipitation, and the amount of COX2 labeled with [$^{14}$C] was confirmed.

Figure 6:
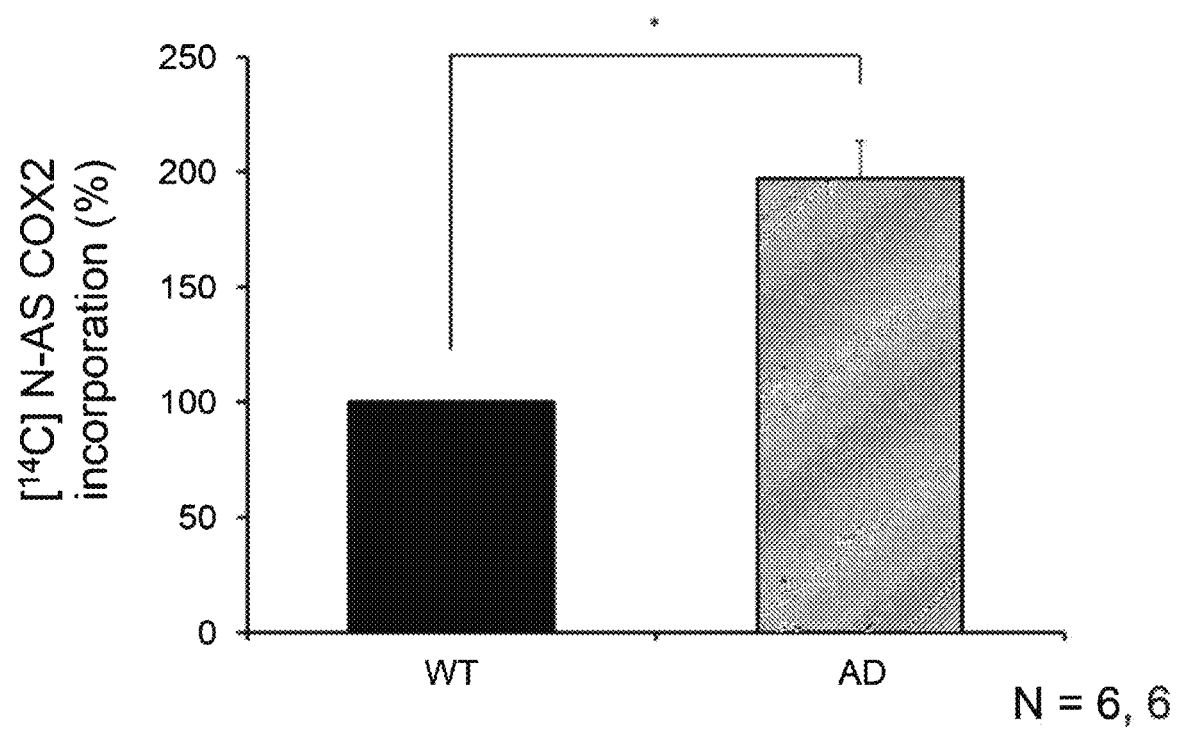
FIG. 6 illustrates a result of confirming the degree of binding of the COX2 protein and [$^{14}$C] in microglia isolated from the brain after administration of [$^{14}$C]N-acetyl sphingosine to 5-month-old wild-type or APP/PS1 mice (WT: wild type, AD: Alzheimer's animal model).

The result thereof was illustrated in FIG. 6.

As can be seen in FIG. 6, it was confirmed that the [$^{14}$C]-labeled COX2 was increased in the Alzheimer's animal model compared to a control (WT).

Therefore, it can be determined that the compounds of the present invention can be used for diagnosis or prognosis prediction of various diseases caused by overexpression of the COX2 protein, including Alzheimer's.

7. Confirming that COX2 Expression of Cancer Cells, Neuroblastoma SH-SY5Y, was Increased.

According to previous studies, it has been reported that the expression level of the COX2 protein was increased in cancer cells (J Cell Physiol. 2019 May; 234(5):5683-5699).

Accordingly, the present inventors confirmed whether the COX2 expression was increased in cancer cells.

Figure 7:
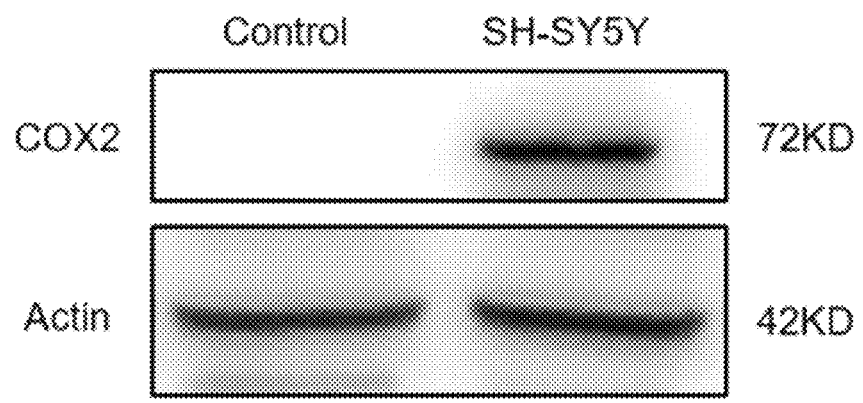
FIG. 7 illustrates results of confirming and quantifying through Western blot that the expression of the COX2 protein is increased in a neuroblastoma cell line (neuroblastoma SH-SY5Y).
Figure 7:
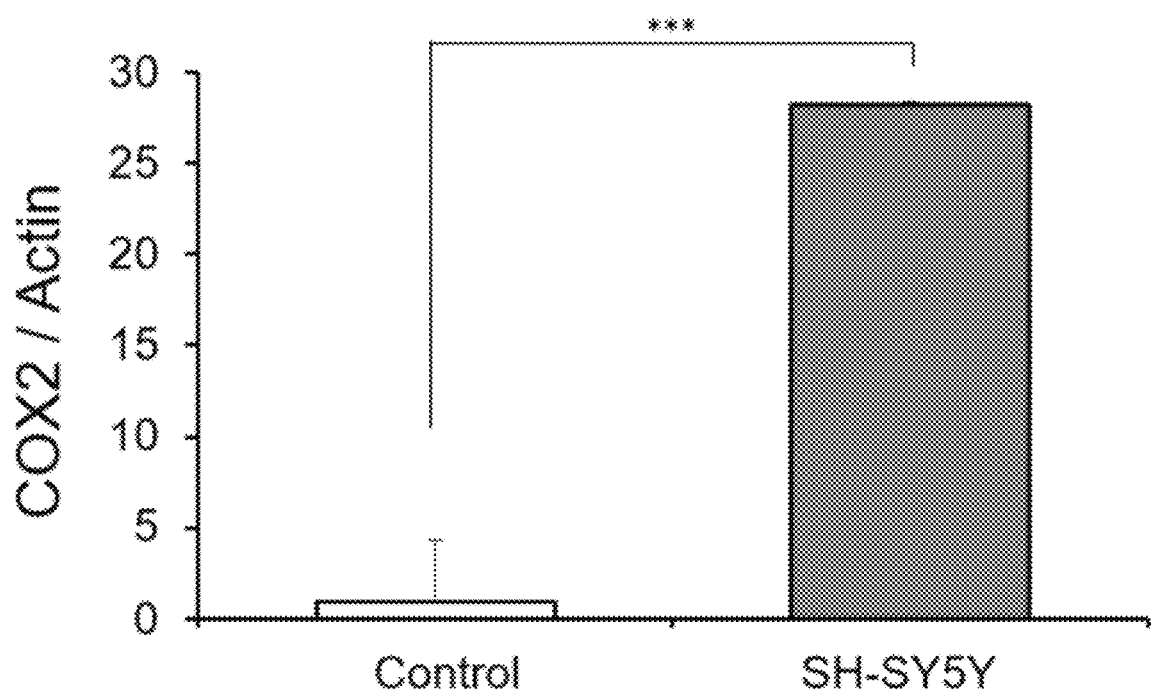

As a result, it was confirmed that the COX2 expression of the cancer cells, neuroblastoma SH-SY5Y was significantly increased compared to a control (normal nerve cells) as illustrated in FIG. 7.

Through the results, it was confirmed that the expression of COX2 was increased in cancer cells, and it was determined that the compounds of the present invention having very excellent direct binding activity with the COX2 protein may be useful for diagnosis or prognosis prediction of cancer.

8. Confirming that COX2 Expression of Cancer Cells, Neuroblastoma SH-SY5Y, was Increased by Using the Compound of the Present Invention The present inventors confirmed that the expression of the COX2 protein in cancer cells, neuroblastoma SH-SY5Y was increased in "Experimental Result 7", and then attempted to confirm whether the increased expression of the COX2 protein may be directly detected in the cancer cells using the compounds of the present invention.

In other words, [$^{14}$C]N-acetyl sphingosine ([$^{14}$C]N-AS), in which carbon of N-AS strongly binding to COX2 was substituted with an isotope, was treated to the cancer cells (2 µCi). After 1 hour, the COX2 was isolated from the control and the cancer cells, neuroblastoma SH-SY5Y by immunoprecipitation, and the amount of COX2 labeled with [$^{14}$C] was confirmed.

Figure 8:
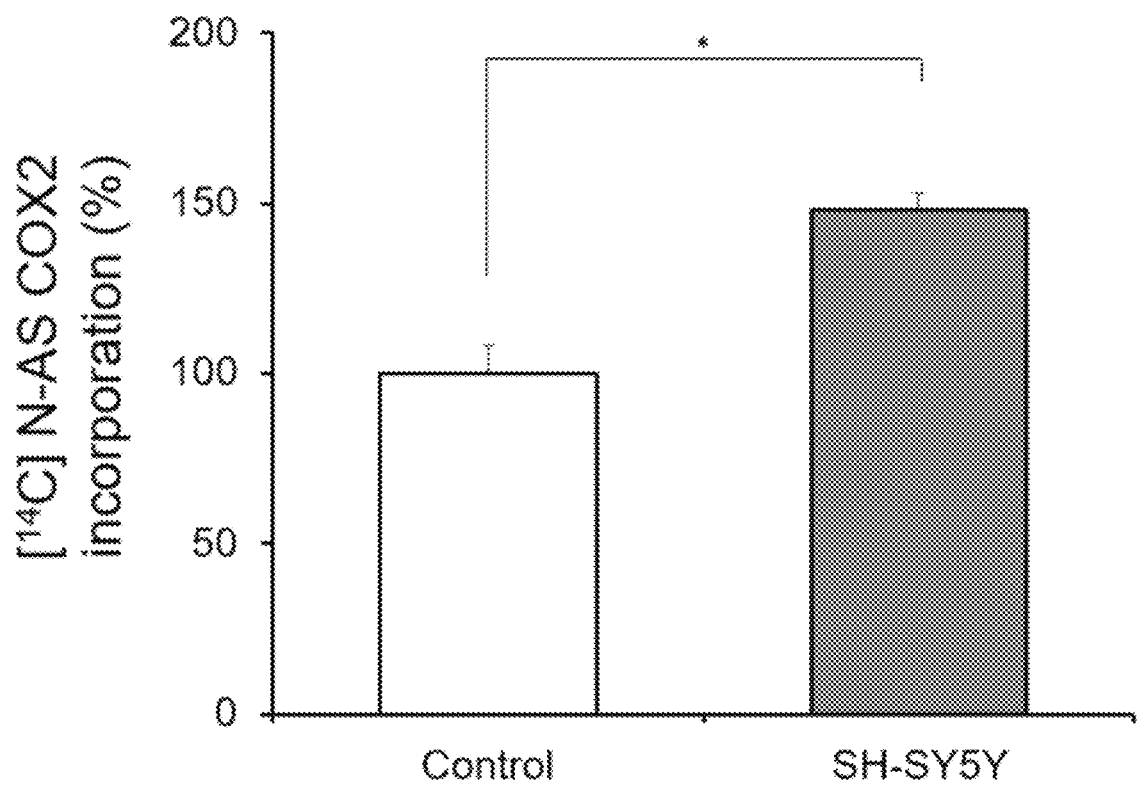
FIG. 8 illustrates a result showing a result of detecting an amount of [$^{14}$C] binding to the COX2 protein by collecting cells after treatment with [$^{14}$C]N-acetyl sphingosine in a neuroblastoma cell line (neuroblastoma SH-SY5Y) for 1 hour.

The result thereof was illustrated in FIG. 8.

As can be seen in FIG. 8, it was confirmed that the [$^{14}$C]-labeled COX2 was increased in the cancer cells, neuroblastoma SH-SY5Y compared to a control.

Therefore, it can be determined that the compounds of the present invention can be used for diagnosis or prognosis prediction of various diseases caused by overexpression of the COX2 protein, including Alzheimer's and cancer.

INDUSTRIAL APPLICABILITY

The compounds provided in the present invention not only have very excellent binding force with COX2, but also have very high blood-brain barrier (BBB) permeability, and can be very useful in diagnosing and predicting prognosis of diseases associated with COX2 overexpression including neurodegenerative diseases. Therefore, the compounds of the present invention have very excellent industrial applicability.

What is claimed is:

1. An analysis method comprising: measuring binding between a compound and a cyclooxygenase 2 (COX2) protein defined by SEQ ID NO: 1 in a sample obtained from a subject, wherein the compound is a compound defined by Chemical Formula 1:

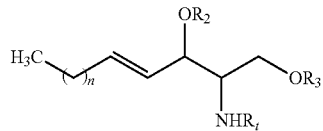

Chemical Formula 1 wherein,
at least one atom of the compound defined by Chemical Formula 1 is a radioactive isotope, $R_1$ is hydrogen or $C_1$-$C_7$ alkylcarbonyl, $R_2$ and $R_3$ are each independently hydrogen, $C_1$-$C_7$ alkylcarbonyl, or

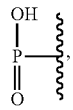

and n is an integer of 5 to 15, and wherein at least one of $R_1$, $R_2$, and $R_3$ is a $C_1$-$C_7$ alkylcarbonyl.

2. The method of claim 1, wherein the compound contains a functional group that interacts with the COX2 protein at one or more amino acids selected from the group consisting of N181, T564, S567, and S565.

3. The method of claim 1, wherein the binding is a hydrogen bond with at least one amino acid selected from the group consisting of N181, T564 and S567 or a nucleophilic acyl substitution reaction with S565.

4. The method of claim 3, wherein at least one atom of the $C_1$-$C_7$ alkylcarbonyl of at least one of $R_1$, $R_2$, and $R_3$ is a radioactive isotope.

5. The method of claim 3, wherein the compound defined by Chemical Formula 1 is labeled with one or more radioactive isotopes selected from the group consisting of $^2$H, $^3$H, $^{11}$C, $^{13}$C, $^{14}$C, $^{13}$N, $^{15}$N, $^{15}$O, and $^{17}$O.

6. The method of claim 3, wherein the compound defined by Chemical Formula 1 above is selected from compounds defined by the following Chemical Formulas 2 to 11:

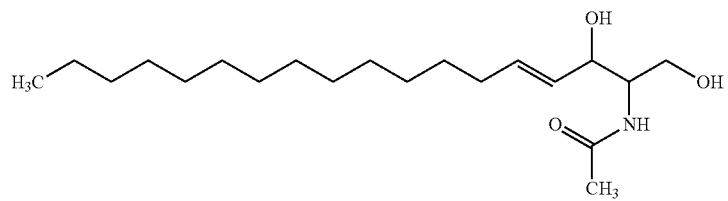
[Chemical Formula 2]
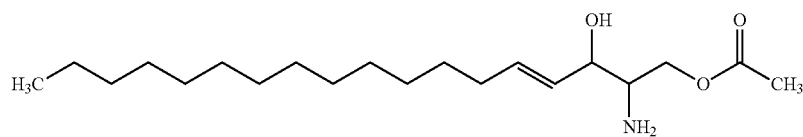
[Chemical Formula 3]
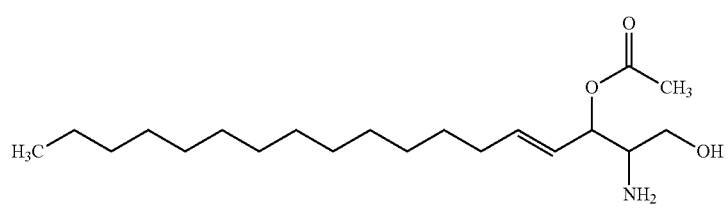
[Chemical Formula 4]
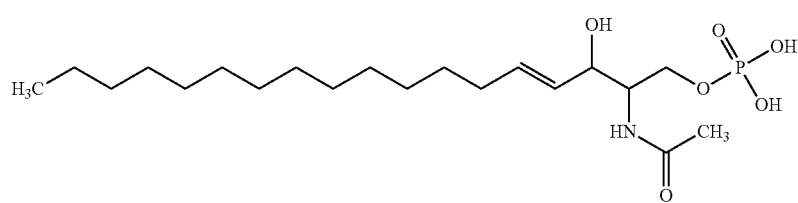
[Chemical Formula 5]
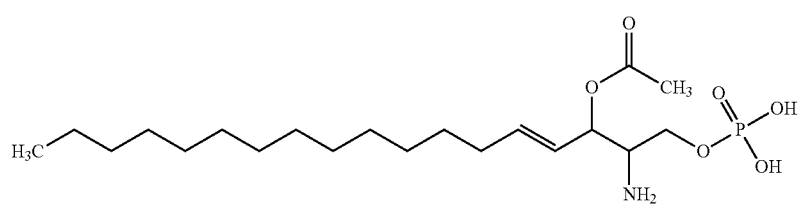
[Chemical Formula 6]
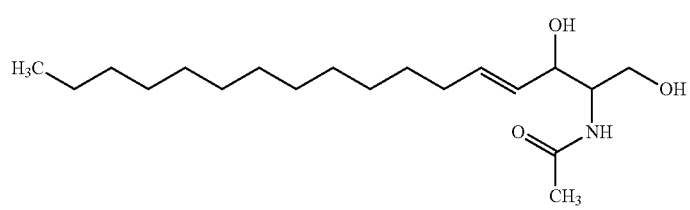
[Chemical Formula 7]
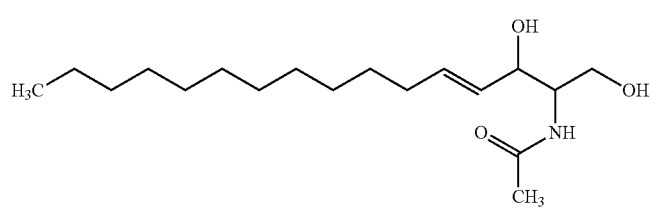
[Chemical Formula 8]
[Chemical Formula 9]
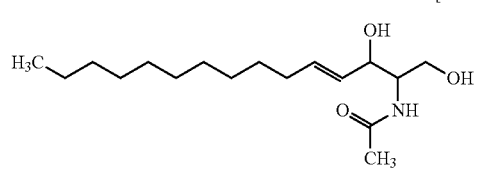
[Chemical Formula 10]
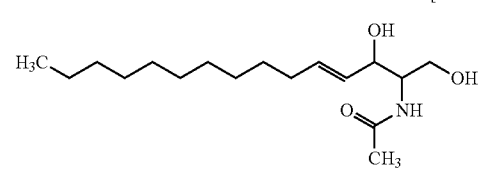

-continued
[Chemical Formula 11]
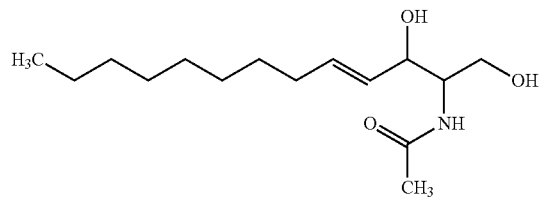
and, wherein in all compounds defined by Chemical Formulas 2 to 11, an atom of an acetyl group is a radioactive isotope.
7. The method of claim 1, wherein the measuring is done by photographic film or scintillation counters.
* * * * *

SEQUENCE LISTING

<160> NUMBER OF SEQ ID NOS: 1

<210> SEQ ID NO 1
<211> LENGTH: 604
<212> TYPE: PRT
<213> ORGANISM: Artificial Sequence
<220> FEATURE:
<223> OTHER INFORMATION: Cyclooxygenase 2(Human)

<400> SEQUENCE: 1

```
Met Leu Ala Arg Ala Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Ile Pro Phe Leu Arg Asn
                85                  90                  95

Ala Ile Met Ser Tyr Val Leu Thr Ser Arg Ser His Leu Ile Asp Ser
                100                 105                 110

Pro Pro Thr Tyr Asn Ala Asp Tyr Gly Tyr Lys Ser Trp Glu Ala Phe
            115                 120                 125

Ser Asn Leu Ser Tyr Tyr Thr Arg Ala Leu Pro Pro Val Pro Asp Asp
        130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
```

-continued

```
                355                 360                 365
Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600
```